(12) United States Patent  
Shea et al.

(10) Patent No.: US 11,605,186 B2  
(45) Date of Patent: Mar. 14, 2023

(54) ANCHORED KERNEL SCATTER ESTIMATE

(71) Applicant: ACCURAY INC., Sunnyvale, CA (US)

(72) Inventors: Jacob Shea, Madison, WI (US); Chuanyong Bai, Solon, OH (US)

(73) Assignee: Accuray, Inc., Sunnyvale, CA (US)

( * ) Notice: Subject to any disclaimer, the term of this patent is extended or adjusted under 35 U.S.C. 154(b) by 2 days.

(21) Appl. No.: 17/363,959

(22) Filed: Jun. 30, 2021

(65) Prior Publication Data

US 2023/0013818 A1 Jan. 19, 2023

(51) Int. Cl.
*A61B 5/00* (2006.01)
*G06T 11/00* (2006.01)
*A61B 6/06* (2006.01)
*A61B 6/00* (2006.01)

(52) U.S. Cl.
CPC .............. *G06T 11/005* (2013.01); *A61B 6/06* (2013.01); *A61B 6/5282* (2013.01)

(58) Field of Classification Search
CPC .... G06T 11/003; G06T 11/005; G06T 11/006; G06T 2210/41; A61B 6/032; A61B 6/5282; A61B 2090/3762; A61B 5/0035; A61B 8/15; A61B 5/0073; G01N 21/47; G01N 2223/419; G01N 23/046
See application file for complete search history.

(56) References Cited

U.S. PATENT DOCUMENTS

| | | | |
|---|---|---|---|
| 4,190,773 A | 2/1980 | Braden et al. | |
| 5,615,279 A | 3/1997 | Yoshioka et al. | |
| 6,233,478 B1 | 5/2001 | Liu | |
| 6,307,909 B1 | 10/2001 | Flohr et al. | |
| 7,050,528 B2 | 5/2006 | Chen | |
| 7,108,421 B2 | 9/2006 | Gregerson et al. | |

(Continued)

FOREIGN PATENT DOCUMENTS

| | | | |
|---|---|---|---|
| DE | 102006007058 A1 | 7/2007 | |
| DE | 102012200150 A1 * | 7/2013 | ........... A61B 6/4233 |

(Continued)

OTHER PUBLICATIONS

Anas, et al., High-quality 3D correction of ring and radiant artifacts in flat panel detector-based cone beam volume CT imaging, Phys. Med. Biol., 2011, pp. 6495-6519, vol. 56.

(Continued)

*Primary Examiner* — Don K Wong
(74) *Attorney, Agent, or Firm* — Calfee, Halter & Griswold LLP

(57) ABSTRACT

A radiological imaging apparatus is provided that includes a radiation source for emitting radiation, a radiation detector positioned to receive radiation emitted by the radiation source and generate radiation data, wherein the radiation data comprises a primary component and a secondary component, and a data processing system. The data processing system is configured to apply image transforms to the primary component using generating functions, build a scatter model basis using the transforms, adjust parameters in the scatter model to fit scatter using the scatter model basis, generate an estimated scatter image by using the fitted scatter model, and modify the radiation data using the scatter image to decrease the scatter in the radiation data thereby generating a scatter corrected image.

21 Claims, 17 Drawing Sheets

(56) References Cited

U.S. PATENT DOCUMENTS

| | | |
|---|---|---|
| 7,302,038 B2 | 11/2007 | Mackie et al. |
| 7,336,759 B2 | 2/2008 | Nukui |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 11,337,668 B2 | 5/2022 | Yu et al. |
| 2003/0007601 A1 | 1/2003 | Jaffray et al. |
| 2003/0076927 A1 | 4/2003 | Nakashima et al. |
| 2004/0068169 A1 | 4/2004 | Mansfield et al. |
| 2004/0091079 A1 | 5/2004 | Zapalac |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1 | 5/2006 | Gohno |
| 2006/0262894 A1 | 11/2006 | Bernhardt et al. |
| 2007/0127621 A1 | 6/2007 | Grass et al. |
| 2007/0189444 A1 | 8/2007 | Van Steven-Daal et al. |
| 2008/0103834 A1 | 5/2008 | Reiner |
| 2008/0112532 A1 | 5/2008 | Schlomka |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2009/0304142 A1 | 12/2009 | Ruimi et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0142312 A1 | 6/2011 | Toth et al. |
| 2011/0176717 A1 | 7/2011 | Siren et al. |
| 2011/0255656 A1 | 10/2011 | Star-Lack et al. |
| 2011/0255657 A1 | 10/2011 | Noordhoek |
| 2012/0014582 A1 | 1/2012 | Schaefer et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0169652 A1 | 6/2014 | Vic et al. |
| 2015/0297165 A1 | 10/2015 | Tanaka et al. |
| 2015/0305696 A1 | 10/2015 | Yamakawa et al. |
| 2016/0005194 A1 | 1/2016 | Schretter et al. |
| 2016/0016009 A1 | 1/2016 | Manzke et al. |
| 2016/0120486 A1 | 5/2016 | Goto et al. |
| 2016/0220844 A1 | 8/2016 | Paysan et al. |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0192978 A1 | 7/2018 | Naylor et al. |
| 2018/0345042 A1 | 12/2018 | Voronenko et al. |
| 2019/0099149 A1 | 4/2019 | Li |
| 2020/0016432 A1 | 1/2020 | Maolinbay |
| 2020/0121267 A1 | 4/2020 | Deutschmann |
| 2020/0402644 A1 | 12/2020 | Zhou et al. |
| 2021/0165122 A1 | 6/2021 | Morton |

FOREIGN PATENT DOCUMENTS

| | | | |
|---|---|---|---|
| EP | 1062914 A1 | 12/2000 | |
| EP | 2383702 A1 | 11/2011 | |
| JP | 09218939 A | 8/1997 | |
| JP | 2004136021 A | 5/2004 | |
| JP | 2008036275 A | 2/2008 | |
| WO | 2005112753 A2 | 12/2005 | |
| WO | 2006078386 A2 | 7/2006 | |
| WO | 2010014288 A1 | 2/2010 | |
| WO | 2010099621 A1 | 9/2010 | |
| WO | 2015103184 A1 | 7/2015 | |
| WO | 2018156968 A1 | 8/2018 | |
| WO | 2018183748 A1 | 10/2018 | |

OTHER PUBLICATIONS

Bootsma, et al., Spatial frequency spectrum of the x-ray scatter distribution in CBCT projections, Med. Phys., Nov. 2013, pp. 111901-1-111901-15, vol. 40, No. 11.

International Search Report and Written Opinion from PCT/US2021/039824 dated Mar. 4, 2022.

International Search Report and Written Opinion from PCT/US2021/042906 dated Mar. 21, 2022.

Rührnschopf, et al., A general framework and review of scatter correction methods in cone beam CT. Part 2: Scatter estimation approaches, Med. Phys. Sep. 2011, pp. 5186-5199, vol. 38, No. 9.

Yang, et al., Scattering estimation for cone-Beam CT Using Local Measurement Based on Compressed Sensing, IEEE transactions on Nuclear Science, Mar. 2018, pp. 941-949, vol. 65, No. 3.

Clackdoyle, et al., Data consistency conditions for truncated fanbeam and parallel projections, Med. Phys. Feb. 2015, pp. 831-845, vol. 42, No. 2.

Defrise, et al., A solution to the long-object problem in helical cone-beam tomography, Physics in Medicine and Biology, 2000, pp. 623-643, vol. 45.

Hsieh, et al., A novel reconstruction algorithm to extend the CT scan field-of-view, Med. Phys., Sep. 2004, pp. 2385-2391, vol. 31, No. 9.

International Search Report and Written Opinion from PCT/US2019/063071 dated Mar. 18, 2020.

International Search Report and Written Opinion from PCT/US2019/063073 dated Apr. 3, 2020.

International Search Report and Written Opinion from PCT/US2019/063074 dated Mar. 23, 2020.

International Search Report and Written Opinion from PCT/US2019/063076 dated Mar. 16, 2020.

International Search Report and Written Opinion from PCT/US2019/063077 dated Mar. 16, 2020.

International Search Report and Written Opinion from PCT/US2019/063078 dated Oct. 8, 2020.

International Search Report and Written Opinion from PCT/US2019/063080 dated Mar. 16, 2020.

International Search Report and Written Opinion from PCT/US2019/063083 dated Mar. 16, 2020.

International Search Report and Written Opinion from PCT/US2019/063085 dated Mar. 16, 2020.

International Search Report and Written Opinion from PCT/US2019/063086 dated Nov. 16, 2020.

International Search Report and Written Opinion from PCT/US2019/063087 dated Apr. 3, 2020.

Invitation to Pay Additional Fees from PCT/US2019/063086 dated Mar. 26, 2020.

Kang, et al., Accurate positioning for head and neck cancer patients using 2D and 3D image guidance, Journal of Applied Clinical Medical Physics, Mar. 2011, pp. 1-14, vol. 12, No. 1.

Katsevich, A., An improved exact filtered backprojection algorithm for spiral computed tomography, Advances in Applied Mathematics, 2004, pp. 691-697, vol. 32.

Kudo, et al., Exact and approximate algorithms for helical cone-beam CT, Physics in Medicine and Biology, 2004, pp. 1-26, vol. 49, No. 13.

Kunze, et al., Cone beam reconstruction with displaced flat panel detector, 10th International Meeting on Fully Three-Dimensional Image Reconstruction in Radiology and Nuclear Medicine, 2009, pp. 138-141.

Li, et al., Scatter kernel estimation with an edge-spread function method for cone-beam computed tomography imaging, Physics in Medicine and Biology, pp. 6729-6748, vol. 51.

Liu, et al., X-Ray micro-CT with a displaced detector array: Application to helical cone-beam reconstruction, Medical Physics, Oct. 2003, pp. 2758-2761, vol. 30, No. 10.

(56) References Cited

OTHER PUBLICATIONS

Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo, et al., A new scheme for view-dependent data differentiation in fan-beam and cone-beam computed tomography, Physics in Medicine and Biology, 2007, pp. 5593-5414, vol. 52.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,161 dated Sep. 13, 2021, 18 pages.
Office Action from U.S. Appl. No. 16/694,230 dated Apr. 1, 2021, 6 pages.
Ramamurthi, et al., Region of Interest Cone Beam Tomography With Prior CT Data, Conference Record of the 37th Asilomar Conference on Signals, Systems, & Computers, Nov. 2003, pp. 1924-1927, vol. 2.
Restriction Requirement from U.S. Appl. No. 16/694,210 dated Jun. 10, 2021, 6 pages.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Schäfer, et al., FBP and BPF reconstruction methods for circular X-ray tomography with off-center detector, Med. Phys., Jul. 2011, pp. S85-S94, vol. 38, No. 7.
Siewerdsen, et al., A simple, direct method for x-ray scatter estimation and correction in digital radiography and cone-beam CT, Med. Phys., Jan. 2006, pp. 187-197, vol. 33, No. 1.
Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Wang, et al., A General Cone-Beam Reconstruction Algorithm, IEEE Transactions on Medical Imaging, Sep. 1993, pp. 486-496, vol. 12, No. 3.
Wang, Ge, X-Ray micro-CT with a displaced detector array, Medical Physics, Jul. 2002, pp. 1634-1636, vol. 29, No. 7.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Invitation to Pay Additional Fees from PCT/US2022/035500 dated Oct. 13, 2022, 14 pages.

* cited by examiner

1500

1302

1304

ANCHORED KERNEL SCATTER ESTIMATE

CROSS-REFERENCE TO RELATED APPLICATIONS

This application is related to U.S. patent application Ser. No. 16/694,145, entitled "MULTIMODAL RADIATION APPARATUS AND METHODS," filed Nov. 25, 2019, now issued as U.S. Pat. No. 11,154,269, and U.S. patent application Ser. No. 16/694,148, entitled "APPARATUS AND METHODS FOR SCALABLE FIELD OF VIEW IMAGING USING A MULTI-SOURCE SYSTEM," filed Nov. 25, 2019, now issued as a U.S. Pat. No. 11,413,002, both of which are incorporated by reference herein in their entirety.

FIELD OF THE INVENTION

Aspects of the disclosed technology relate to improving quality during radiological image processing, including, for example, reducing noise and artifacts associated with scatter and scatter correction, and, more particularly, to processing a scatter-corrected image as a non-scatter-corrected component and a scatter-only component.

BACKGROUND

Tomography is a noninvasive, radiological imaging technique that is used to generate cross-sectional images of a three dimensional (3D) object without superimposing tissues. Tomography can be categorized into transmission tomography, such as computed tomography (CT) and emission tomography like single photon emission computed tomography (SPECT) and positron emission tomography (PET). CT is a technique based on x-ray transmission through a patient to create images of sections of the body. Photon emission computed tomography and positron emission tomography provide 3D image information about radionuclides injected into the patient showing the metabolic and physiological activities within an organ.

In tomographic scans, projections are acquired from many different angles around the body by one or more rotating detectors (along with rotating radiation sources in CT). These data are then reconstructed to form 3D images of the body. For example, the reconstruction of tomographic images can be achieved via filtered back projection and iterative methods.

The quality of the final image is limited by several factors. Examples include attenuation and scatter photons, detection efficiency, spatial resolution of the collimator-detector system, etc. These factors can cause poor spatial resolution, low contrast, and/or high noise levels. Image data processing (e.g., filtering) techniques can be used to improve the quality of the image.

In CT, including cone-beam CT, the primary signal detected by a detector element represents the x-rays that come out from the tube, penetrate the patient body, and reach the detector. The x-rays in the primary signal travel along the x-ray paths that connect the tube focal point of the tube to detecting elements. The scatter signal detected by the same element also represents the x-rays that are scattered from other x-ray paths into the elements. The primary signal allows the reconstruction of CT images. The scatter signal, however, can degrade the CT images, both quantitatively and qualitatively.

Scatter in various radiological imaging modalities, including CT and cone-beam CT, can account for a significant portion of the detected photons. Scatter can negatively impact image quality, including contrast, uniformity, and quantitative accuracy. Consequently, scatter measurement, estimation, and correction are applicable to data processing and image reconstruction, including in the context of image-guided radiation treatment (IGRT). IGRT can make use of medical imaging technology, such as CT, to collect images of a patient before, during, and/or after treatment.

BRIEF SUMMARY

In one variation, a radiological imaging apparatus is provided that includes a radiation source for emitting radiation, a radiation detector positioned to receive radiation emitted by the radiation source and generate radiation data, wherein the radiation data comprises a primary component and a secondary component, and a data processing system. The data processing system is configured to apply image transforms to the primary component using generating functions, build a scatter model basis using the transforms, adjust parameters in the scatter model to fit scatter using the scatter model basis, generate an estimated scatter image by using the fitted scatter model, and modify the radiation data using the scatter image to decrease the scatter in the radiation data thereby generating a scatter corrected image.

The radiation source may comprise a rotating x-ray source emitting a radiation beam. The radiation detector may comprise an x-ray detector positioned to receive the radiation from the x-ray source. The apparatus may further comprise a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer.

Estimating the scatter component of the radiation data may be based on measured scatter data in at least one shadow region. Modifying the radiation data using the scatter image to decrease the scatter in the radiation data may comprise subtracting the scatter image from the radiation data.

The generating functions may comprise at least one of a narrow-angle kernel, a wide-angle kernel, a gaussian kernel, a filter or filter bank, an orthonormal basis, a Fourier Transform, a wavelet basis, and a continuous wavelet transform. The scatter model may comprise a convolutional neural net. The scatter model may comprise a singular value decomposition or an eigenvalue decomposition. The scatter model may comprise at least one of a least squares, weighted least squares, conjugate-gradient least squares, and nonlinear optimization technique. The scatter model basis may comprise an orthonormal basis. The scatter model basis may comprise Gaussian kernels. The scatter model basis may comprise at least one of asymmetric Gaussian kernels, symmetric Gaussian kernels and Gaussian kernels with non-zero skewness. Separating the radiation data into the primary and scatter components may comprise filtering the radiation data. Separating the radiation data into the primary and scatter components may comprise segmenting the radiation data. Adjusting parameters in the scatter model to fit scatter may comprise an iterative analysis of the radiation data. The iterative analysis may analyze a segmented image comprising primary radiation data. The data processing system may be configured to at least one of offset the radiation data, normalize the radiation data, correct the radiation data, and weight one or more portions of the radiation data. The apparatus may further include dynamic positioning of collimators to manipulate the radiation emitted by the radiation source prior to the radiation detector receiving the radiation.

Variations may include a method of processing radiation data acquired by a radiological imaging apparatus. The method includes receiving the radiation data, separating the radiation data into the primary and secondary components, applying image transforms to the primary component using generating functions, building a scatter model basis using the transforms, adjusting parameters in the scatter model to fit scatter in the at least one of the primary and secondary components using the scatter model basis, generating an estimated scatter image by using the fitted scatter model, and modifying the radiation data using the scatter image to decrease the scatter in the radiation data thereby generating a scatter corrected image.

Features that are described and/or illustrated with respect to one variation may be used in the same way or in a similar way in one or more other variations and/or in combination with or instead of the features of the other variations.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, variations of the invention are illustrated, which, together with a general description of the invention given above, and the detailed description given below, serve to exemplify variations of this invention. It will be appreciated that illustrated element boundaries (e.g., boxes, groups of boxes, or other shapes) in the figures represent one variation of boundaries. In some variations, one element may be designed as multiple elements or that multiple elements may be designed as one element. In some variations, an element shown as an internal component of another element may be implemented as an external component and vice versa. Furthermore, elements may not be drawn to scale.

DETAILED DESCRIPTION

Figure 1:
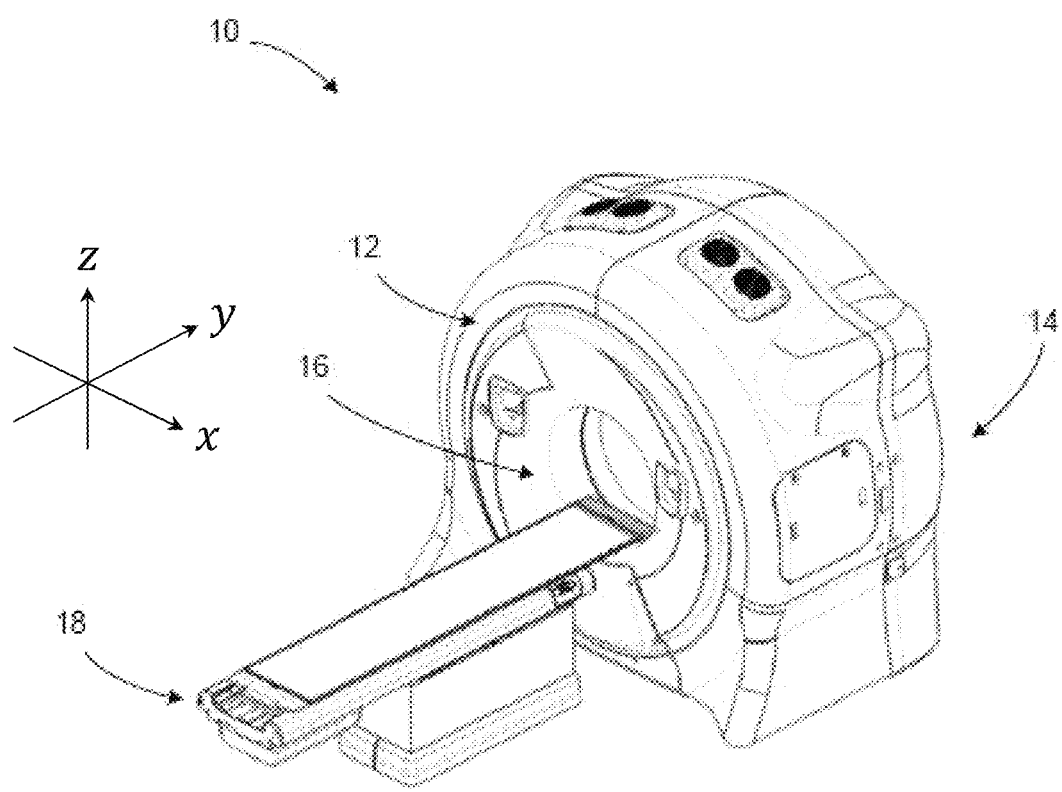
FIG. 1 is a perspective view of an exemplary imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), field-programmable gate arrays (FPGAs), graphics processing units (GPUs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

In a CT scan, the x-ray reference data (I0) that is the signal when there is no patient (and patient table). When the raw or patient data (Id) is acquired, the ratio of the flux to the signal at each detector element is computed. The log of the ratio is the line integral of the linear attenuation of the patient along the corresponding x-ray path if the patient data has only the primary signal (Pr). Subsequently, CT images can be reconstructed from the line integrals measured by all the detector elements in many angles around the patient.

Since the detected signal includes both the primary (Pr) and scatter signal (Sc), where Id=Pr+Sc, the direct calculation of the ratio of the reference to the detector signal, I0/Id, is no longer the integral of the linear attenuation of the patient along the x-ray path (I) since it is contaminated by a scatter component (Sc) in the signal. Explicitly, the correct line integral should be I=log(I0/Pr). Including scatter, the calculated ratio is shown in equation 1:

$$Id = \log(I0/Id), \quad (1)$$

where Id=Pr+Sc.

Scatter Sc has a positive value. Without scatter correction, the calculated line integral will be less than the true line integral without Sc. Reconstruction using the contaminated line integral Id will lead to quantitative bias in the image, and qualitatively, reduce contrast and introduce artifacts to the images.

In order to handle the scatter issue above, clinical CT systems can use hardware approaches to minimize scatter during data acquisition upfront and once data is acquired, as well as apply software approaches to correct the residual scatter in the measured data. The latter can be referred to as scatter correction.

The principle of scatter correction is to estimate the scatter (Sc_est) and remove or subtract the estimated scatter from the patient data and calculate the corrected line integral according to equation 2:

$$I_{corr} = \log\left(\frac{I_0}{I_d - Sc\_est}\right) = \log\left(\frac{I_0}{Pr + (Sc - Sc\_est)}\right) \quad (2)$$

If the scatter estimate (Sc_est) accurately represents the scatter component in the measured data, then equation 2 leads to a line integral that will facilitate an accurate CT image reconstruction.

Scatter correction increases the noise in the calculated line integral. This leads to increased noise in the reconstructed image. The variance (noise) of the line integral without scatter correction is shown in equation 3:

$$Var\_Id = \left(\frac{1}{Id}\right)^2 \times Var\_Id, \quad (3)$$

where Var_Id is the variance of the measured patient data Id, assuming variance of I0 is 0.

The variance of the line integral after scatter correction is shown in equation 4:

$$Var\_corr = \left(\frac{1}{I_d - Sc\_est}\right)^2 Var\_Id + \left(\frac{1}{I_d - Sc\_est}\right)^2 Var\_Sc\_est \quad (4)$$

where Var_Sc_est is the variance (noise) of the estimated scatter (Sc_est) assuming the noise of the estimated scatter is independent from the noise of the measure data.

Comparing the noise of the scatter corrected line integral in equation 4 and that of the non-scatter corrected line integral in equation 3, shows that, even if the scatter estimate (Sc_est) has no noise, the noise of the calculated line integral is amplified by a factor shown in equation 5:

$$\left(\frac{I_d}{I_d - Sc\_est}\right)^2 \quad (5)$$

Noise amplification represented by equation 5 increases when the percentage of scatter in the measured data increases. For example, if 50% of the measured data is scatter, then the noise is amplified by a factor of 4. In cone-beam CT systems that use anti-scatter grids, residual scatter can be 30% of the data. Equation 5 predicts a noise amplification of around 2. Cone-beam CT with flat-panel detectors without anti-scatter grids, scatter can be more than 50% of the total measured data. The larger the patient, the greater the scatter.

Noise reduction approaches for scatter correction could: (a) reduce the noise of the estimated scatter, which corresponds to reducing the noise in the second term in the right-hand-side of equation 4; (b) reduce noise in the scatter corrected raw data or line integral; (c) model scatter in an iterative reconstruction as an additive term to the estimated primary and compare the sum of the estimated primary and scatter to the measured data; (d) regularize noise in reconstruction; and/or (e) filter/de-noise the scatter corrected image.

While all these approaches may have benefits, they also have drawbacks. For approach (a), even if one could make the scatter with little noise, the noise would still be amplified by the factor shown in equation 5. This factor can be very significant in CT scans with a significant amount of scatter, especially for cone-beam CT with a large imaging field-of-view and without anti-scatter grids. Approach (b) not only carries this drawback of approach (a), but also may lose signal (resolution and contrast). This is because the raw data is filtered due to noise reduction. Approach (c) requires a more sophisticated reconstruction algorithm and longer reconstruction time. It also has limited noise reduction. Approach (d) can be challenged by the regularization design. Consider the scatter corrected image as a combination of a non-scatter corrected component and a scatter correction component. The non-scatter corrected component has lower noise than the scatter correction component. Therefore, applying regularization to the entire image tends to over-regularize the low-noise non-scatter corrected component. Post reconstruction image processing (filtering)/de-noise in approach (e) shares the same challenge as in approach (d).

In variations disclosed herein, the scatter corrected image can be treated as the combination of two components. The first component is the non-scatter corrected component and the second is the scatter only component. The line integral in equation 2 can be rewritten as the sum of two components as shown in equation 6:

$$I_{corr} = \log\left(\frac{I_o}{I_d}\right) + \left[\log\left(\frac{I_0}{I_d - \text{Sc\_est}}\right) - \log\left(\frac{I_o}{I_d}\right)\right] \quad (6)$$

The first term in equation 6 is the line integral without scatter correction. The second term in the square brackets is the scatter correction component of the line integral. For analytical reconstruction, the reconstruction of the corrected line integral is equivalent to the reconstruction of the two terms separately to generate two images, followed by the summation of the two images to obtain the final scatter corrected image. The image reconstructed from the first term is equivalent to the conventional non-scatter corrected image (noSC image). The image reconstructed from the second term can be referred to as the scatter-only image (Scatter-only image). Equation 7 shows these components explicitly:

CT image=noSC image+Scatter-only image  (7)

The scatter estimate (Sc_est) can be removed from the patient data using equation (7). The Scatter-only image carries the scatter correction related noise and artifacts. The noSC image is of much lower noise than the Scatter-only image, and the overall CT image is the combination of the two.

Conventional noise reduction associated with scatter correction, whether in raw data, in the reconstruction process, or post reconstruction, essentially operates on the combined noSC and Scatter-only components of the image, despite that the two components have very different noise. Suppressing noise in the Scatter-only component may lead to over smoothing (hence resolution degradation) of the noSC component. An approach that minimizes resolution degradation may not be effective to suppress the noise associated with scatter correction.

The variations described herein achieve improved image quality after scatter correction. The improvements include, for example, both sufficient noise reduction and low resolution degradation. In these variations, treating the Scatter-only image separately from and differently than the noSC image can reduce noise and artifacts associated with scatter and scatter correction. A stronger noise suppression data processing technique (e.g., filter) can be applied to the higher noise Scatter-only image to improve noise reduction. Concurrently, a lighter noise suppression data processing technique (e.g., filter) can be applied to the noSC image to minimize the resolution loss. In this and other ways, the two image components in equation 7 may be improved independently. The combined final image (e.g., CT image) can have an improved compromise of noise reduction and resolution preservation.

In some variations, using the noSC image to guide the noise reduction of the high noise Scatter-only image can have further benefits. Since the noSC image has lower noise than the Scatter-only image, it can guide noise reduction of the Scatter-only image. This guiding can include determining the filter kernel and any associated parameters. Guided noise reduction of the Scatter-only image can lead to Scatter-only images with noise similar to or even lower than the noSC image. Edges in the noSC images can provide reliable edge-preserving guidance of the data processing (e.g., filtering) of the Scatter-only image. The combined final image (e.g., CT image) can have a noise level similar to that in the noSC image, while edge-preservation is improved.

In variations, the two components of equation 6 may be reconstructed differently. For example, a higher resolution filter (kernel) may be used to reconstruct the noSC component while a more smoothing filter (lower resolution kernel) may be used to reconstruct the Scatter-only component.

The following flow charts and block diagrams illustrate exemplary configurations and methodologies associated with scatter correction and/or image generation. The exemplary methodologies may be carried out in logic, software, hardware, or combinations thereof. In addition, although the procedures and methods are presented in an order, the blocks may be performed in different orders, including series and/or parallel. Thus, the steps below, including imaging, image-based pre-delivery steps, and treatment delivery, although shown sequentially, may be executed simultaneously, including in real-time. Further, additional steps or fewer steps may be used.

Variations of the disclosed technology relate to correcting scatter in imaging data, including utilizing patient data (Id) and a scatter estimate (Sc_est) from an imaging scan. The imaging scan may be performed by any radiological imaging apparatus associated with the type of scan, including x-ray, CT, CBCT, SPECT, PET, MR, etc. These methods can be used for scatter correction in the imaging data from these imaging scans, for example, for noise and artifact reduction. Although CT scanners and cone-beam CT scanners are highlighted in several exemplary variations, this technique can also be applied to image reconstruction/data processing based on the removal of unwanted counts/signals from the original counts to generate corrected images, such as, for example, scatter correction in SPECT, PET, MR, SPECT/CT, PET/CT, PET/MR, etc.

In variations, the imaging scan may be performed using a dedicated imaging apparatus or an imaging apparatus integrated with a radiotherapy delivery apparatus. For example, a radiotherapy delivery device can make use of an integrated low-energy radiation source for CT for use in conjunction with or as part of IGRT. In particular, for example, a radiotherapy delivery device and associated methods can combine a low-energy collimated radiation source for imaging in a gantry using rotational (e.g., helical or step-and-shoot) image acquisition along with a high-energy radiation source for therapeutic treatment, as described in U.S. patent application Ser. No. 16/694,145, entitled "MULTIMODAL RADIATION APPARATUS AND METHODS," filed Nov. 25, 2019, and in U.S. patent application Ser. No. 16/694,148, entitled "APPARATUS AND METHODS FOR SCALABLE FIELD OF VIEW IMAGING USING A MULTI-SOURCE SYSTEM," filed Nov. 25, 2019, both of which are incorporated by reference herein in their entirety. In these variations, the low-energy radiation source (e.g., kilovolt (kV)) can produce higher quality images than via use of the high-energy radiation source (e.g., megavolt (MV)) for imaging.

The imaging data acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with variations, the imaging apparatus collimates a radiation source, including, for example, into a cone beam or a fan beam using, for example, a beamformer. In one variation, the collimated beam can be combined with a gantry that continuously rotates while the patient moves, resulting in a helical image acquisition.

Detectors (with various row/slice sizes, configurations, dynamic range, etc.), scan pitch, and/or dynamic collimation are additional features in variations, including to selectively expose portions of the detector and selectively define active readout areas, as discussed in detail below.

The imaging apparatus and method can provide selective and variable collimation of a radiation beam emitted by the source of radiation, including adjusting the radiation beam shape to expose less than the entire active area of an associated radiation detector (e.g., a radiation detector positioned to receive radiation from the radiation source). Exposing only a primary region of the detector to direct radiation allows shadowed regions of the detector to receive only scatter. Scatter measurements in the shadow region (and in some variations measurements in the penumbra region) of the detector can be used to estimate scatter in the primary region of the detector receiving projection data.

Figure 2:
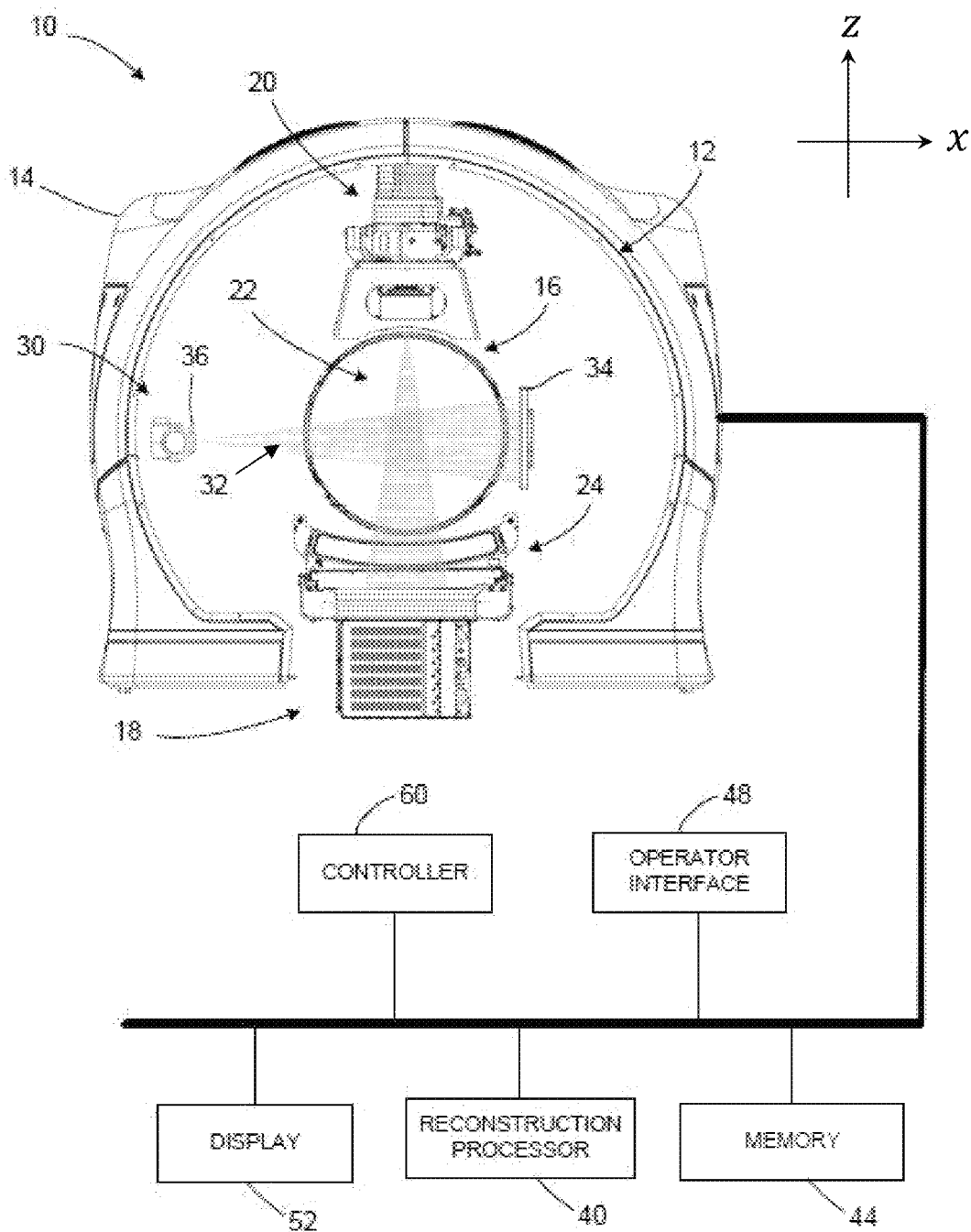
FIG. 2 is a diagrammatic illustration of an imaging apparatus integrated into an exemplary radiotherapy device in accordance with one aspect of the disclosed technology.

With reference to FIGS. 1 and 2, an exemplary imaging apparatus 10 (which can include, e.g., an x-ray imaging apparatus) is shown. It will be appreciated that the imaging apparatus 10 may be associated with and/or integrated into a radiotherapy device (as shown in FIG. 2) that can be used for a variety of applications, including, but not limited to IGRT. The imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. The rotatable gantry 12 defines a gantry bore 16 into and through which a patient can be moved and positioned for imaging and/or treatment. In accordance with one variation, the rotatable gantry 12 is configured as a slip ring gantry to provide continuous rotation of an imaging radiation source (x-ray) and an associated radiation detector while providing sufficient bandwidth for the high-quality imaging data received by the detector.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The apparatus 10 is capable of volume-based and planar-based imaging acquisitions. For example, in variations, the device 10 may be used to acquire volume images and/or planar images and execute the associated processing methods described above.

As shown in FIG. 2, the imaging apparatus 10 includes a source of imaging radiation 30 coupled to or otherwise supported by the rotatable gantry 12. The source of imaging radiation 30 emits a radiation beam (indicated generally as 32) for generating high-quality images. In this variation, the source of imaging radiation is an x-ray source 30, configured as a kilovoltage (kV) source (e.g., a clinical x-ray source having an energy level in the range of about 20 kV to about 150 kV). The imaging radiation source can be any type of transmission source suitable for imaging. Other imaging transmission sources can be used interchangeably in various other variations.

The imaging apparatus 10 also can include another source of radiation 20 coupled to or otherwise supported by the rotatable gantry 12. In accordance with one variation, the source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam). Generally, the source of radiation 20 has a higher energy level (peak and/or average, etc.) than the source of imaging radiation 30. Although FIGS. 1 and 2 depict an x-ray imaging apparatus 10 with a radiation source 30 mounted to a ring gantry 12, other variations may include other types of rotatable imaging apparatuses, including, for example, C-arm gantries and robotic arm-based systems.

A detector 34 (e.g., two-dimensional flat detector or curved detector) can be coupled to or otherwise supported by the rotatable gantry 12. The detector 34 (e.g., x-ray detector) is positioned to receive radiation from the source of imaging radiation 30 and can rotate along with the source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient.

A collimator or beamformer assembly (indicated generally as 36) is positioned relative to the imaging source 30 to selectively control and adjust a shape of a radiation beam 32 emitted by the source 30 to selectively expose a portion or region of the active area of the detector 34. The beamformer can also control how the radiation beam 32 is positioned on the detector 34. For example, in one variation, 3-4 centimeters of projection image data may be captured with each readout, with about 1-2 centimeters of unexposed detector area on one or each side, which may be used to capture scatter data.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

The therapeutic radiation source 20 may be mounted, configured, and/or moved into the same plane or a different plane (offset) than the imaging source 30. In some variations, scatter caused by simultaneous activation of the radiation sources 20, 30 may be reduced by offsetting the radiation planes.

When integrated with a radiotherapy device, imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, x-ray, CT, CBCT, MR, PET, SPECT, and/or 3D rotational angiography (3DRA) data, and/or any information obtained from these or other imaging modalities. In some variations, the imaging apparatus 10 can track in-treatment patient, target, or ROI motion.

A reconstruction processor 40 can be operatively coupled to detectors 24, 34. In one variation, the reconstruction processor 40 is configured to generate patient images based on radiation received by detectors 24, 34 from the radiation sources 20, 30, as discussed above. It will be appreciated that the reconstruction processor 40 can be configured to carry out the methods described herein. The apparatus 10 can also include a memory 44 suitable for storing information, including, but not limited to, data processing and reconstruction algorithms and software, including filters and data processing/filter parameters, imaging parameters, image data from a prior or otherwise previously-acquired image (e.g., a planning image), treatment plans, and the like.

The imaging apparatus 10 can include an operator/user interface 48, where an operator of the imaging apparatus 10 can interact with or otherwise control the imaging apparatus 10 to provide input relating to scan or imaging parameters and the like. The operator interface 48 can include any suitable input devices, such as a keyboard, mouse, voice-activated controller, or the like. The imaging apparatus 10 can also include a display 52 or other human-readable element to provide output to the operator of the imaging apparatus 10. For example, the display 52 can allow the operator to observe reconstructed patient images and other information, such as imaging or scan parameters, related to operation of the imaging apparatus 10.

As shown in FIG. 2, the imaging apparatus 10 includes a controller (indicated generally as 60) operatively coupled to one or more components of the apparatus 10. The controller 60 controls the overall functioning and operation of apparatus 10, including providing power and timing signals to the imaging source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the imaging source 30, a beamformer 36 controller, a controller coupled to the detector 24 and/or the detector 34, and the like. In one variation controller 60 is a system controller that can control other components, devices, and/or controllers.

In variations, the reconstruction processor 40, the operator interface 48, the display 52, the controller 60 and/or other components may be combined into one or more components or devices.

The apparatus 10 may include various components, logic, and software. In one variation, the controller 60 comprises a processor, a memory, and software. By way of example and not limitation, an imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one variation, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with imaging apparatus 10.

Imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

There are many determinants of image quality (e.g., imaging source focal spot size, detector dynamic range, etc.). A limitation of many imaging techniques and image quality is scatter. Various approaches can be used to reduce scatter. One approach is to use an anti-scatter grid (which collimates the scatter). However, it can be problematic to implement a scatter grid on a kV imaging system, including for motion tracking and correction. As discussed above, accurately estimating scatter in the projection data is necessary to improve the quality of the image data. In variations, scatter in the projection data acquired in a primary region of the detector 34 can be estimated based on data measured in shadow regions (and penumbra regions) of the detector 34.

Figure 3:
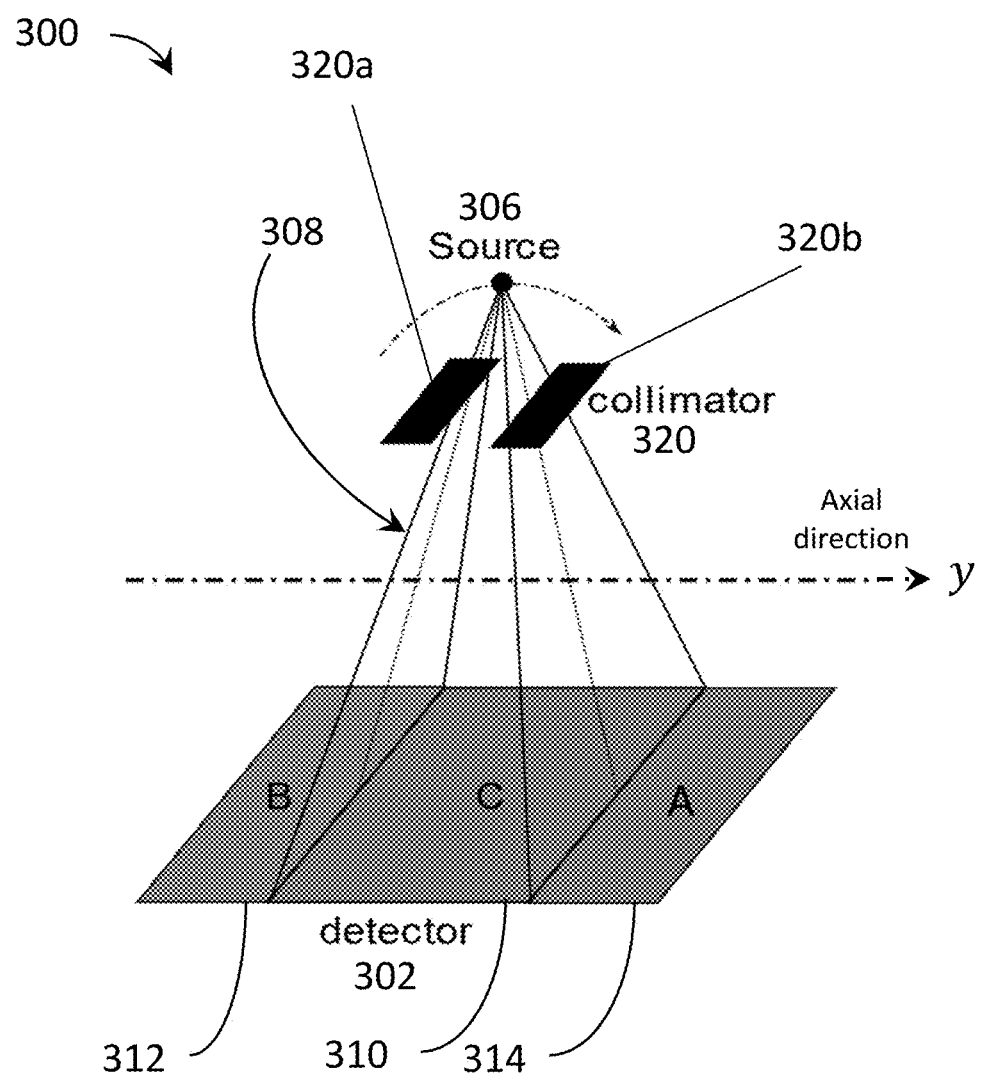
FIG. 3 is a diagrammatic illustration of an exemplary collimated projection onto a detector.

FIG. 3 is a diagrammatic illustration of an exemplary collimated projection 300 onto a detector 302. Rotating radiation source 306 (e.g., x-ray) is shown emitting radiation beam 308 exposing a primary or center (C) region 310 of the detector 302 to direct radiation from source 306 (e.g., through a target) as the source 306 rotates around the y-axis. Patient support (not shown) motion can be in an axial (longitudinal) direction along the y-axis, including as part of a scan as described above. Detector 302 also has a back (B) shadow region 312 and a front (A) shadow region 314 that are blocked from direct exposure to the radiation beam 308 by a beamformer/collimator 320. Beamformer/collimator 320 is configured to adjust a shape and/or position of the radiation beam 308 emitted by the source 306 onto detector 302. The shadowed regions 312, 314 will only receive scattered radiation.

The collimator 320 opening is configured in such a way that the back (B) end 312 and the front (A) end 314 of the detector 302 in the axial or longitudinal direction (along the patient table direction or y-axis) are not illuminated with direct radiation 308. These back (B) 312 (in the negative longitudinal direction along the rotation y-axis) and front (A) 314 (in the positive longitudinal direction along the rotation y-axis) shadow regions can be utilized for scatter measurement since they do not receive direct radiation. For example, a detector 302 readout range can be configured to read out all or a portion of the data in the one or more shadow regions 312, 314 and use the data for scatter estimation in the primary region 310. The primary or center (C) region 310 receives both direct projections and scatter.

In variations, a data processing system (including, e.g., processor 40) can be configured to receive measured projection data in the primary region 310 and measured scatter data in at least one shadow region 312, 314, then determine an estimated scatter in the primary region 310 based on the measured scatter data in at least one shadow region 312, 314. In some variations, determining the estimated scatter in the primary region 310 during a current rotation can be based on the measured scatter data in at least one shadow region 312, 314 during the neighboring (previous and/or subsequent) rotations. In other variations, measured data from penumbra region(s) (bordering the primary and shadow regions) may also be used for scatter estimation.

Various techniques and methods can utilize different scan geometries, detector positioning, and/or beamformer window shapes. In some variations, the detector may also be offset in the transverse direction.

Figure 4:
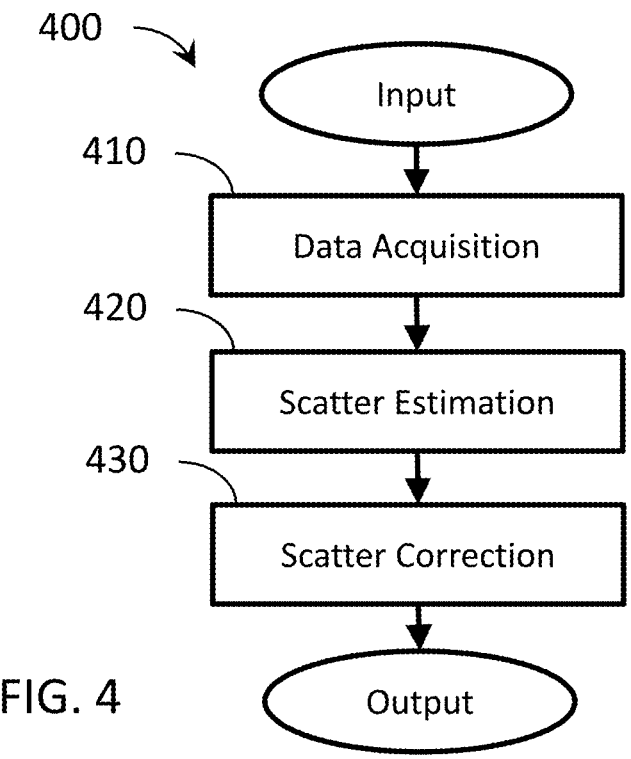
FIG. 4 is a flow chart depicting an exemplary method of scatter correction.

FIG. 4 is a flow chart depicting an exemplary method 400 of scatter estimation and correction, such as those described above. Inputs can include any optional prior data and/or scan designs. In this variation, step 410 includes data acquisition. For example, during rotation of a radiation source projecting a collimated radiation beam towards a target and radiation detector, the method measures projection data (primary+scatter) in a central (primary) region of a radiation detector and measures scatter using a front shadow peripheral region and/or a back shadow peripheral region of the detector. Data acquisition in step 410 can also include adjusting a shape/position of the radiation beam with the beamformer before and/or during the scan and/or adjusting a readout range (including determining the active region).

Next, step 420 includes scatter estimation. For example, the method estimates the scatter in the projection data from the central (primary) region using the scatter measurement from the shadow region(s). Then, step 430 includes scatter correction, which can include any of the two-component techniques described above. Output includes scatter corrected projection data suitable for imaging. Various variations can utilize different scan geometries, detector positioning/active areas, beamformer positioning/window shapes, etc.

Figure 5:
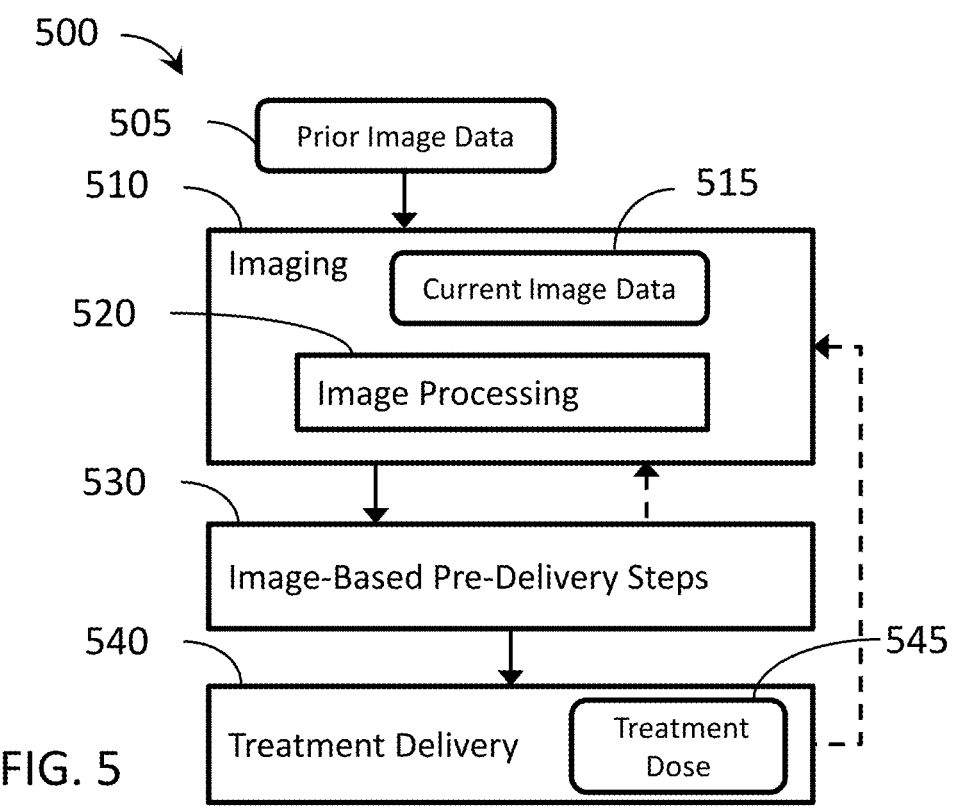
FIG. 5 is a flow chart depicting an exemplary method of IGRT using an imaging apparatus within a radiotherapy device.

FIG. 5 is a flow chart depicting an exemplary method 500 of IGRT using a radiotherapy device (including, e.g., imaging apparatus 10). Prior image data 505 of the patient may be available for use, which may be a previously-acquired planning image, including a prior CT image. Prior data 505 can also include treatment plans, phantom information, models, a priori information, etc. In some variations, prior image data 505 is generated by the same radiotherapy device, but at an earlier time. At step 510, imaging of a patient is performed using a source of low-energy radiation (e.g., kV radiation from x-ray source 30). In one variation, imaging comprises a helical scan with a fan or cone beam geometry. Step 510 can produce high-quality (HQ) image(s) or imaging data 515 using the scatter estimation and correction techniques described above. In some variations, image quality may be adjusted to improve a balance between image quality/resolution and dosage. In other words, not all images need to be of the highest quality or image quality may be adjusted to improve or trade off a balance between image quality/resolution and image acquisition time. Imaging step 510 can also include image/data processing to generate patient images based on the imaging data (e.g., in accordance with the methods described above). Although image processing step 520 is shown as part of imaging step 510, in some variations image processing step 520 is a separate step, including where image processing is executed by separate devices.

Next, at step 530, one or more image-based pre-delivery steps, discussed below, are performed based at least in part on the imaging data 515 from step 510. As discussed in more detail below, step 530 can include determining various parameters associated with the therapeutic treatment and (subsequent) imaging planning. In some variations, image-based pre-delivery steps (530) may require more imaging (510) before treatment delivery (540). Step 530 can include adapting a treatment plan based on the imaging data 515 as part of an adaptive radiotherapy routine. In some variations, image-based pre-delivery steps 530 may include real-time treatment planning. Variations may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 540, therapeutic treatment delivery is performed using a source of high-energy radiation (e.g., MV radiation from therapeutic radiation source 20). Step 540 delivers a treatment dose 545 to the patient according to the treatment plan. In some variations, the IGRT method 500 may include returning to step 510 for additional imaging at various intervals, followed by image-based pre-delivery steps (530) and/or treatment delivery (540) as required. In this manner the high-quality imaging data 515 may be produced and utilized during IGRT using one apparatus 10 that is capable of adaptive therapy. As mentioned above, steps 510, 520, 530, and/or 540 may be executed simultaneously, overlapping, and/or alternating.

In variations, whether the imaging data is generated using a dedicated imaging apparatus or an imaging apparatus integrated with a radiotherapy delivery apparatus, the various methods described above can be utilized for scatter correction.

In one variation, a CT apparatus includes a rotating x-ray source and an x-ray detector obtain a set of raw data (e.g., Id) for CT image generation, hardware and/or software to measure and/or generate a set of scatter data (e.g., Sc_est) to compensate/correct the scatter contamination in the raw data. A non-scatter corrected image is reconstructed from the raw data, and a scatter only image is reconstructed from the scatter data. In this variation, the raw data can be used to compute non-scatter corrected line integrals for the reconstruction of a non-scatter corrected CT image. The scatter data can be used to compute scatter-only line integrals based on equation 6 for the reconstruction of a scatter-only image. The non-scatter-corrected image and the scatter-only image are processed independently with the latter being filtered more heavily due to the higher noise. The processed non-scatter-corrected image and the processed scatter-only image can be combined to create the final CT image with scatter correction.

In another variation, volume image subtraction may be used to generate the scatter-only image. Here, the scatter data is used together with the raw data to generate scatter-corrected line integrals for the reconstruction of a scatter-corrected image. The raw data can be used to compute non-scatter-corrected line integrals to reconstruct a non-scatter-corrected image. The non-scatter corrected image can be subtracted from the scatter-corrected image to obtain the scatter-only image. The non-scatter-corrected image and the scatter-only image are processed independently with the latter being filtered more heavily due to the higher noise. The processed non-scatter-corrected image and the processed scatter-only image can be combined together to create the final CT image with scatter correction.

In variations, the non-scatter-corrected image can be used to guide the processing of the scatter-only image to achieve effective noise and artifact reduction of the scatter-only image while preserving the edges in the image. For example, the filter can be a Gaussian filter that uses the voxel difference in the non-scatter-corrected image to determine the kernel weights of the scatter-only image filter. In this manner, the edge information in the non-scatter-corrected images is used to preserve the corresponding edges in the scatter-only images. The non-scatter-corrected image can also be used in more advanced edge-preserving processing schemes to enhance the processing of the scatter-only image. For example, processing the scatter-only image can be based on the anisotropic differential filter parameters obtained in the non-scatter-corrected images.

In another variation, the non-scatter-corrected image and the scatter-only image can be reconstructed using different reconstruction schemes. For example, the non-scatter-corrected image can be reconstructed using a higher resolution kernel than the scatter-only image and the scatter-only image can be reconstructed using a customized streak artifact reduction algorithm. The scatter-only image can be reconstructed using a different grid to speed up the reconstruction time. For example, if the non-scatter-corrected image reconstruction uses a matrix of 512×512, the scatter-only image reconstruction can use a 256×256 matrix for reconstruction to speed up the reconstruction time. The reconstructed scatter-only image can then be resampled to the same grid as the non-scatter-corrected image. The non-scatter-corrected image can then be used to guide the processing of the scatter-only image. The resulting scatter-only image can be combined with the non-scatter-corrected image to create the final image with scatter correction.

In addition to the CT environment highlighted in several of the exemplary variations, in various other variations, a variety of imaging apparatuses that acquire or generate raw data with scatter (e.g., Id) and the scatter data (e.g., Sc_est), can use the scatter data to correct the raw data, such as in SPECT, PET, etc. Scatter data can be used to modify/correct the line integral where the line integral can be decomposed into a linear combination of the component without scatter correction and the component due to scatter correction similar to equation 6. The non-scatter-corrected image is of lower noise than the scatter-only image. The two images can be reconstructed differently to improve the quality of both and then can be combined to obtain the final image. The reconstructed non-scatter-corrected image and the scatter-only image can be processed independently to improve the quality of both and then can be combined to obtain the final image. The non-scatter-corrected image can also be used as a guiding image to determine the weight of filtering kernels when processing the scatter-only image.

In addition to the variations that utilize the non-scatter-corrected image to guide the processing of the scatter-only image (i.e., operating in the image domain), other variations can operate in the data domain. In these variations, processing of the generated line integral of the scatter-only component can be based on the line integral data of the non-scatter-corrected component as the guiding data to preserve the edges in the scatter-only component. The resulting line integral of the scatter-only component can be reconstructed separately or together with the line integral of the non-scatter-corrected component.

In variations, the raw data (e.g., Id) and the measured scatter data (e.g., Sc_est) are used together to reconstruct a scatter-corrected image and the raw data is used to reconstruct a non-scatter-corrected image using various reconstruction algorithms to obtain the images. In some variations, the reconstruction can be an analytical reconstruction. In some variations, the reconstruction can be an iterative reconstruction. In variations, the scatter only image is processed (including filtering, artifact reduction, etc.) separately from the non-scatter-corrected image, then combined with the non-scatter corrected image to obtain the final image. In some variations, a scatter-only image is generated by subtracting the non-scatter-corrected image from the scatter-corrected image. Furthermore, the non-scatter-corrected image can be used to guide the processing of the scatter-only image for optimal noise and artifact reduction and edge preservation.

Figure 6:
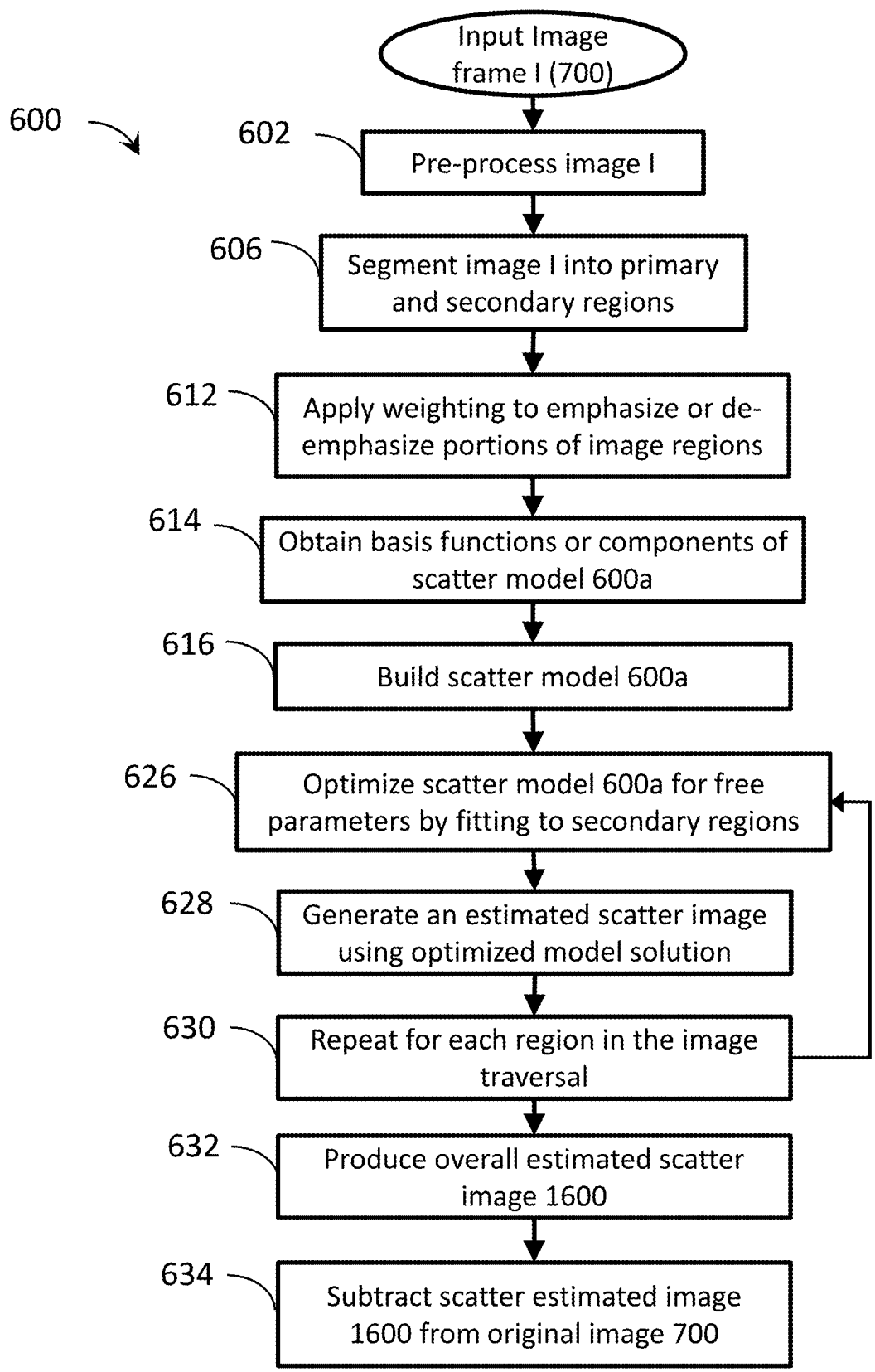
FIG. 6 is a flow diagram of an algorithm 600 that estimates and corrects scatter on an image frame-by-frame using an anchored kernel model.

FIG. 6 is a flow diagram of an algorithm 600 that estimates scatter on an image frame-by-frame using an anchored kernel model. Algorithm 600 may be used to estimate scatter in conjunction with any of the other methods described herein (e.g., methods 400 or 500).

More specifically, algorithm 600 estimates scatter using selective beam blocking in conjunction with a mathematical representation of the scatter.

Suitable mathematical representations of the scatter may include, for example, a Gaussian Mixture Model (GMM). In a GMM representation, Gaussian kernel parameters (e.g., amplitude and/or variance) for a detected beam are estimated by fitting them to measured parameters, including scatter measured from beam blockage. GMMs are useful especially when fitting to a lower spatial-frequency image component that is related to a physical scattering mechanism informed by the projection of the physical object. In a simplified description, GMM can provide a blurring operator with a form of multi-resolution to capture both wide-angle and small angle scattering.

GMMs are only one method of representing scatter. It is to be understood that algorithm 600 is general with respect to the mathematical representation. Other representations that may be used in conjunction with algorithm 600 include those using non-gaussian representations, scatter kernel representations, continuous wavelet transforms, Fourier Transforms, machine learning (e.g., neural nets), etc.

Method 600 employs a collimator (e.g., collimator 320 in FIG. 3) to generate an image I with a secondary A/B and primary C portion. The collimator provides x-ray source-side beam-blocking (e.g., on the side of source 306 shown in FIG. 3). Collimator 320 may have collimator blades 320a and 320b positioned to at least one of the superior, inferior, ipsilateral, and contralateral of the patient view. Although single blades 320a and 320b are shown in FIG. 3, other collimator configurations are possible. For example, patterned beam blocks may be used, as can collimator with other shapes and configurations. Although static beam blocking device positions are shown in FIG. 3, beam blocks and/or collimators dynamically positioned during a scan may be used. Exemplary applications include using dynamic beam collimation to perform region of interest (ROI) volume imaging and radiation dose-reduced target tracking. The collimating blades can be "planned" to follow a target motion search space, or for an ROI reconstruction e.g.

during treatment. For dynamic motion, at each frame instant the shadow positions can be used by the described method.

Such beam collimation can form rectangular shadows 312 and 314 on a flat panel x-ray detector 302. The three regions that may form (e.g., primary C, penumbra (not shown—region between C and A and B), and secondary (i.e., blocked A and B)) may be automatically detected in, for example, a frame-by-frame basis. They may also be known from calibration (e.g., a periodic, prior calibration) of the beam 308 geometry.

Algorithm 600 represents the anchored scatter image estimation using measured secondary data and a scatter basis model 600a (e.g., as a GMM in which the Gaussian component amplitudes are estimated from x-ray absorption data and scatter from a collimation scheme, e.g., as shown in FIG. 3). Although algorithm 600 will be discussed in detail with regard to collimation scheme 300, it is to be understood that the concepts described herein with respect to algorithm 600 are general with regard to the specifics of the collimation scheme and may be employed with collimation schemes other than 300.

Although a specific mathematical model 600a fitting for scatter (e.g., specific GMM configuration and building/fitting protocol) is described below with respect to algorithm 600, algorithm 600 can be configured in a number of different ways. The scatter model can be pre-configured for the imaging system 300 by fitting to measurements of scatter images from phantom (patient, and/or other imaging sample) and gantry 12 angles. This can include, for example, tuning Gaussian variance in a GMM. This fitting can include measured difference, for example, images between a full detector 302 panel exposure and a pencil raster scan or a slit-scan sweep of the source 306 and detector 302. Other types of pre-configuration are possible and within the scope of the present disclosure. However, it is to be understood that such pre-configuration is optional and not necessary in order to implement algorithm 600.

As discussed in more detail below, in certain variations, the model 600a can be configured by solving a system of equations formed by vectorizing image pixels in a masked shadow or "secondary" region (regions A and B in FIG. 3) into a data vector (b). In this configuration based on secondary regions A and B, the unknowns can be, for example, amplitudes of the GMM components (x). Since secondary regions A and B contain pure background scatter signal (i.e., scatter that is not also contaminated with signal from the sample), this configuration can calibrate the GMM for scatter. The primary region C contains both scatter and signal from the sample (e.g., a patient or phantom).

Subsequently, a solvable system matrix A can be formed by mathematically convolving initial model 600a components x with pixels of the primary region (region C of FIG. 3) of the projection image frame I. When convolution begins, model 600a components x may have arbitrary amplitudes or the model 600a components may have been previously configured, as briefly discussed above and in more detail below. The result of the convolution at each pixel in the shadow regions (A and B), corresponding to the order of data vector b, is an element of the system matrix A, an estimate of scatter in the primary region C. Configuring A by any suitable regression algorithm (e.g. by a weighted least squares provides an estimate of GMM model scatter amplitudes).

The result of the convolution at each pixel in the shadow regions (A and B), is an estimate of the scatter at that pixel. The corresponding element of data vector (b) is the measured scatter at that pixel. Matrix A can be resolved by making the estimated scatter matching the measured scatter in data vector (b). Once A is resolved, it can be used to convolve with the data in the primary region C to estimate the estimated scatter in region C. The results can then be used for scatter correction for the primary date in region C. Methods used to resolve the matrix A can be a least square approach, a weighted least square approach, a steepest descent approach, and any other suitable approach for image convolution. Any method of solving for the system, based on the inputs (measured projections including primary and secondary regions), a priori assumptions (e.g., a kernel model such as GMM), with output estimating the scatter image in the primary region. Specific steps in algorithm 600 will be discussed below.

The following description applies algorithm 600 and model 600a to a single image frame. It is to be understood that the steps may be applied to each frame in a multi-frame image. The multiple image frames, once processed and scatter corrected, may be reconstructed to form a 3D representation in a tomography approach. It is to be understood that each step discussed below is optional. Algorithm 600 may be performed without one or more of the steps discussed below. It may also be performed with one or more steps performed in a different order than discussed below. It also may be performed with one or more additional steps not discussed below. All such variations should be considered within the scope of the present disclosure and within the scope of algorithm 600.

At step 602, algorithm 600 may apply corrections (e.g., offsets, bad pixel corrections, and gain normalization) to the input signal, where the input signal is the raw x-ray signal detected by the detector 302. The input signal may be in the form of an image frame I.

In step 602, statistically (or otherwise) anomalous pixels may be identified, changed, and/or eliminated. This may correspond to detecting pixels that differ in intensity from neighboring pixels by a threshold value. These anomalous pixels may result from a number of causes, including defective portions of the detector, interference, stray xrays scattering from other portions of the acquisition setup 300, and/or other problems in data acquisition. Once identified, anomalous pixels may be replaced with averaged (or other valued) pixels.

\In step 602, the image frame I may be altered for quicker and/or more efficient image processing. For example, image I may be down-sampled or otherwise reduced or decomposed in resolution to a larger pixel size or other basis functions. A multi-resolution approach may extract lower spatial-frequency components from the primary image to be used in the method. Doing so can reduce complexity in further processing, potentially speeding up image processing, such as the scatter correction described below. Image downsizing is particularly advantageous for images I or portions of image I that do not have a large spatial variation or spatial frequency. In these cases, downsizing preserves much of the desired information in the original image frame I. Scatter signal image components typically have relatively low spatial variation. For this reason, it can be advantageous to downsize the primary and secondary A/B image portions in this pre-processing step. Doing so may allow quick and accurate processing of scatter signal to correct the image frame I.

Figure 7:
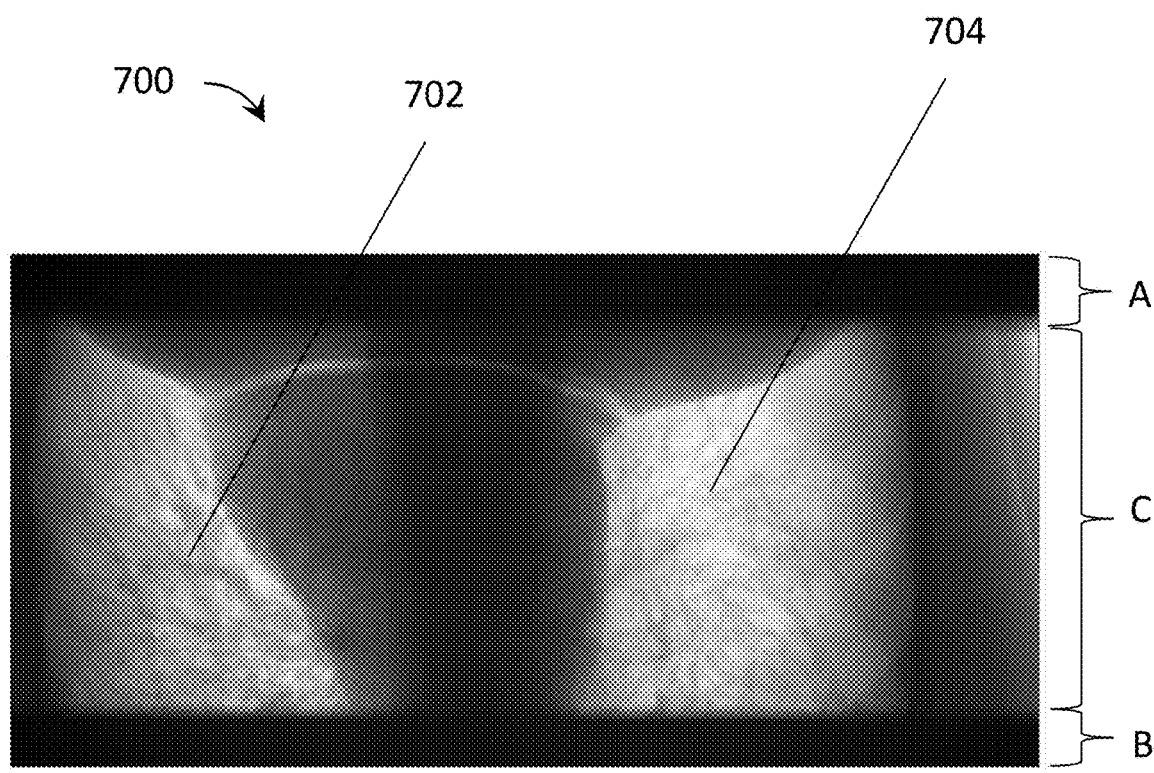
FIG. 7 shows an exemplary processed image 700 according to algorithm 600.

Step 602 results in an image I, such as exemplary processed image 700 shown in FIG. 7. Exemplary image 700 is a projection of a lung phantom in the primary beam C from source 306 after having been pre-processed according to step 602. One can see, for example, two sections 702 and 704 of the lung phantom as bright regions in the primary section C of image 700. Here x-rays through lungs are less attenuated, so the value in lungs are higher (i.e., appear brighter in the image). The primary section C of image 700 corresponds to the image section C of detector 302 shown in FIG. 3. In other words, it is the detected region where a gap in collimator 320 has allowed radiation from source 302 to pass through the lung phantom sample. Regions A and B in image 700, however, represent pure scatter because they correspond to regions where the incident radiation from source 306 has been blocked by collimator blades 320a and 320b.

Each of the shadow or secondary regions A and B on either side of the primary region C in image 700 includes scatter that is common to the primary beam region C. Primary region C may include types of scatter (e.g., scatter from the object, patient, source housing, filtration, collimation apparatus component or bore covers, and various layers of the x-ray detector 302, that is imaged in primary beam region C). Therefore, the pure scatter from secondary regions A/B can be useful for fitting the model 600a to represent much of the scatter present in the entire image 700.

At step 606, image I can be segmented into primary C and secondary (A and B) regions. In this context, "segmenting" means creating two different images from image 700 that can be processed separately. The two images each represent a segment or portion of image 700. In the example, one segmented image may include the portion of image 700 from the secondary portions A/B (FIG. 7). Another segment may include portions of image 700 from the primary portion C. However, these are merely examples and it is to be understood that any suitable, advantageous segmentation of image 700 is possible during this step. The segmenting of step 606 can be performed by any suitable method. Suitable segmenting methods include, for example, applying an imaging mask to image I that enables operating on a sub-region of the image data. Segmenting can be based on x-ray projections images through air, to clearly show the primary, penumbra, and shadow regions of the image. Segmenting may also be possible on a frame by frame basis of the measured object data. Segmenting may be based on a computational model of the imaging geometry and physical source apparatus.

Figure 8A:
FIG. 8A shows an exemplary Boolean mask 800a including primary region C and secondary (shadow) regions A and B that can be employed in for the image segmenting of step 606.

FIG. 8A shows an exemplary Boolean mask 800a including primary region C and secondary (shadow) regions A and B that can be employed in for the image segmenting of step 606. Mask 800a can separate the data of the primary region C from the secondary regions A and B by indexing or other software abstraction. Mask 800a can index all but the primary region C. Mask 800b in FIG. 8B may also be employed for the segmentation step 606. Mask 800b may index all but the secondary regions A and B. In addition to masking, step 606 may include any suitable imaging segmenting routine based on a known imaging geometry (e.g., geometry 300 shown in FIG. 3 including 320 and detector 302) may also be applied in this step. Segmenting may be performed by any method described herein.

Another advantage of image segmenting that images from primary C and secondary A/B may have different characteristics that lend themselves to different processing methods. For example, pixel size or other basis decomposition may be different, filtration may be different, weighting factors may be different in the secondary regions A/B from the primary C. On the other hand, the image segment from primary segment C may include greater spatial resolution and spatially resolved detail than the secondary A/B portion. In that sense, the segmented image corresponding to the primary portion C may benefit from application of imaging processing routines that can advantageously process such detail.

Figure 8B:
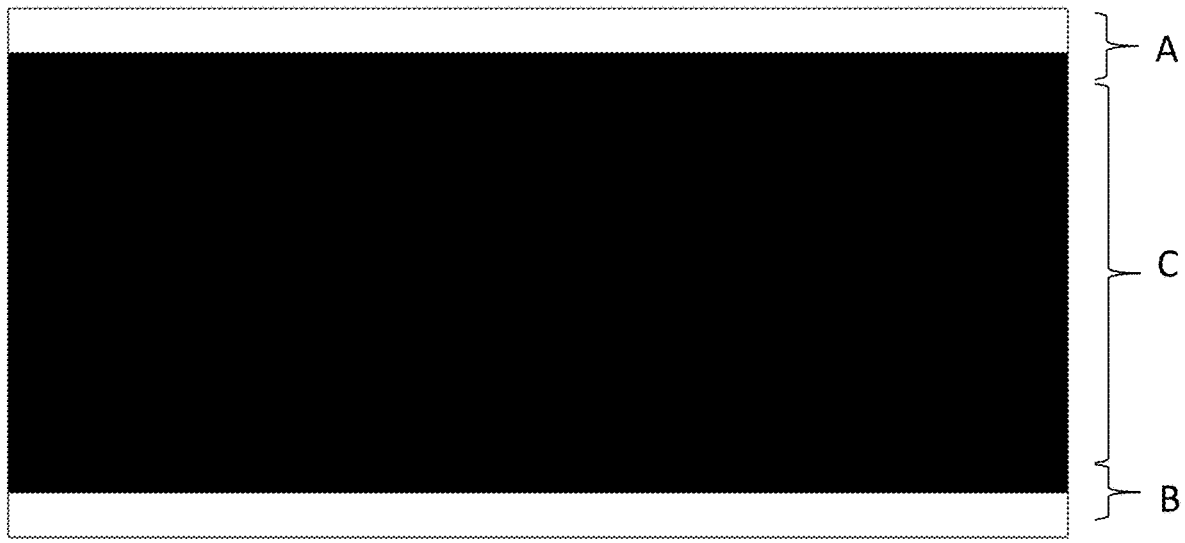
FIG. 8B shows another exemplary mask 800b.
Figure 9:
FIG. 9 shows the separated secondary A/B image 900 that may be created, for example, via application of mask 800b in FIG. 8B.

FIG. 9 shows a separated secondary A/B image 900 that may be created, for example, via application of mask 800b in FIG. 8B. The secondary image 900 includes data for only secondary regions A and B.

Figure 10:
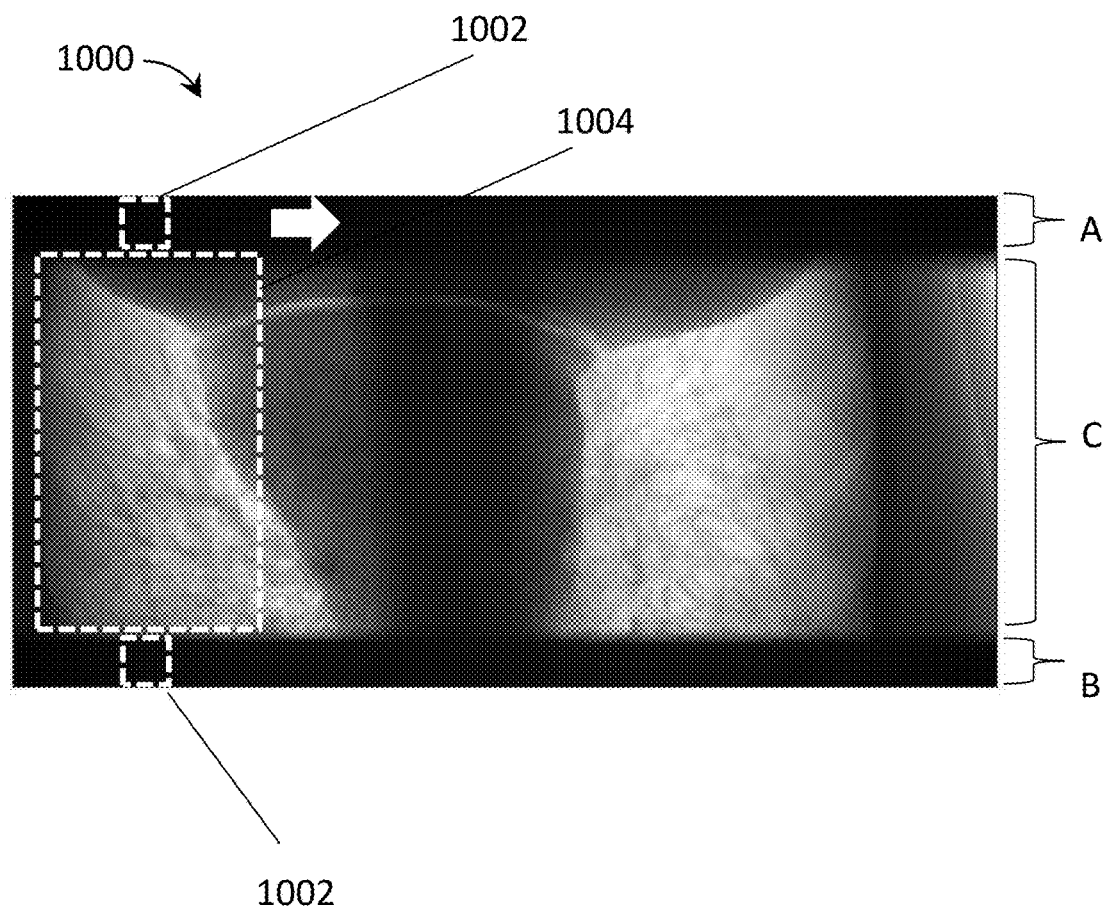
FIG. 10 shows an exemplary primary image 1000 in which the mask 800a has provided a primary region C with data and two secondary regions A and B set to a constant (e.g., zero).

FIG. 10 shows an exemplary image 1000 in which the mask 800a has isolated primary region C. Secondary image 900 and primary image 1000 can be subject to different processing and then re-combined to form a composite image I that has been scatter corrected. The output from the scatter correction may be only the corrected primary region. The secondary region may no longer be actionable in radiograph or CT applications, though a corrected secondary region may be assessed for quality of the estimation.

At step 606, analysis of at least one of images 900 and 1000 is performed. As an example, analysis of image 1000 is shown schematically in FIG. 10. The exemplary analysis includes regions of analysis 1002 in the secondary segments and 1004 in the primary segment. The regions 1002 can be scanned across image 1000 so that the entire image 1000 is analyzed. It is to be understood that the scatter estimation algorithm is making use of primary data from the full image 1000 or from region 1004 and secondary data from the full image 1000 or from region 1002. An advantage of traversing the image 1000 by regions is that the estimated model parameters may vary in the transverse direction, as scatter behavior may vary with ray angle as a function of object thickness or other factors. An advantage of regions 1002 and 1004 may having different widths is that the scatter data in 1002 is contributed to by a wider extent of the object under irradiation.

Image regions 1002 and 1004 can be the focus of an image processing calculation (e.g., vectorization of pixels, determination of max/min, average, Fourier transform, etc.). The calculation may include any suitable processing method of and may combine one or more such methods.

Image regions 1002 and 1004 may be processed concurrently with other image regions (not shown) so that parallel analyses of image 1000 may be performed at once. Alternatively to using image regions, image 1000 may be analyzed in a single step. Processing in step 602 may continue in an iterative fashion with other steps described below. In particular, processing in step 606 may occur until estimation of the full scatter image is complete.

One approach iteratively estimates the scatter data in the secondary segment after scatter correcting the primary segment by the previous estimate. The advantage is that the physical scattering mechanism is related to the attenuation through the object, whereas the raw image data in the primary region also contains scatter signal. In another approach, scatter basis functions could be estimated and corrected from the full image in serial fashion. For example, kernels used in the scattering model 600a may be estimated individually, from higher spatial frequency to lower, or vice versa. More generally, selected basis functions could be estimated individually in an iterative fashion.

At step 612, algorithm 600 may apply weighting to emphasize or de-emphasize certain features of image I. For example, a weighting may be chosen that de-emphasizes the influence of air-only paths on the scatter estimate, or to amplify the relative contribution to the scatter estimate from low image values. Any suitable mathematical operation may be used to weight the image. Examples of suitable operations include image subtraction as well as applying a logarithmic ("log") operator (e.g., a negative logarithmic operator to eliminate portions of the image, etc.). A suitable negative log operator, for example, can transform, for example, a gain-normalized projection frame of image I (or images 900 and 1000) such that high image values (e.g., those received through paths that do not traverse the patient, phantom, or other sample and, therefore, do not include object scatter effects) are attenuated or zeroed.

Figure 11:
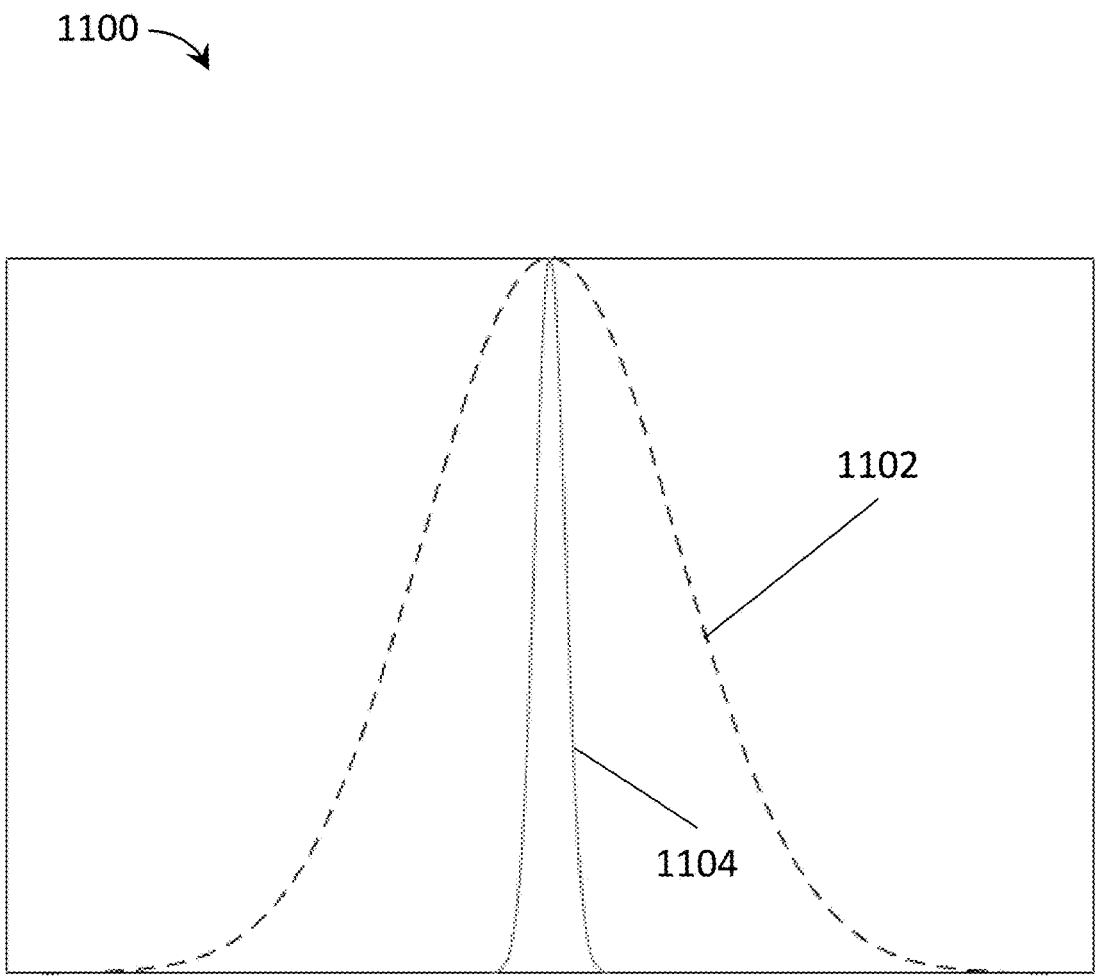
FIG. 11 shows two potential scatter kernels 1102 and 1104 that may be used in the convolution of step 614.

In step 614, algorithm 600 creates basis functions of the model 600a (e.g., GMM) using data from image 1000. FIG. 11 shows two exemplary scatter kernels 1102 and 1104 from the GMM variation that generate scatter model basis functions by convolution with image 1000. It is to be understood that kernels 1102 and 1104 are merely exemplary and any suitable kernel, generating function, or basis decomposition may be used. Any number of scatter kernels may be used in this step. This step may further include any suitable choice of basis function decomposition, and selection of basis functions therein. For example, any gaussian or non-gaussian basis may be used and/or combinations therein. Other bases may also be used in this step, including orthonormal bases, wavelet bases, continuous wavelet transforms, and/or combinations thereof. If kernels are to be used, they may be symmetrical or asymmetrical, skewed or not skewed.

Scatter kernel 1102 is an exemplary wide-angle kernel, while scatter kernel 1104 is an exemplary narrow-angle scatter kernel. Using both a wide angle and narrow angle scatter kernel together may impart geometrically distinct scattering mechanisms to the model 600a. One or more combinations of these and/or other kernel types may further improve the accuracy of the model. More generally, model 600a can include more than one kernel type, and more than two kernels, for more accurate modeling of scatter. Any suitable number of kernels or basis functions may be used in algorithm 600.

In convolution-based variations, the convolution of step 614 can be performed with any suitable mathematical convolution algorithm or integral transform. For example, if a GMM is used in model 600a, convolution may be performed by integrating the product of each basis function of the GMM and the image data over the image. One or more of the basis functions used by the model 600a to represent the image data may be reversed and/or shifted during convolution or filtering. Other suitable convolution processes are possible. Convolution in this step may be accomplished by using a series of convolution steps involving one of more of these convolution processes. Other algorithms. In the region-wise approach using image region 1002, convolution-based variations can be applied to a wider area of the primary region C, then extracting from the output only those narrower primary regions. Scatter from the entire primary region C contributes to the narrower primary regions. Performing convolution in the Fourier domain can provide computational advantage. Generalization to kernel convolution can be via a filter bank or multi-resolution decomposition, for example. Weighting of the filter bank or basis set can be informed or calibrated by physical scattering processes.

Typically, convolution in step 614 will involve the image region data from the primary image C (i.e., segmented image 1000 in FIG. 10) because scatter is generated by the primary beam. This step configures the basis functions of the model 600a. However, in some instances, the convolution step may involve secondary image 900 data as well. The convolution can be applied to the primary C and penumbra areas. It can be assumed that there is little or no primary radiation on the secondary (shadow) regions A/B, and therefore little additional scatter contribution from direct paths from the source to image I pixels in regions A/B.

Figure 12:
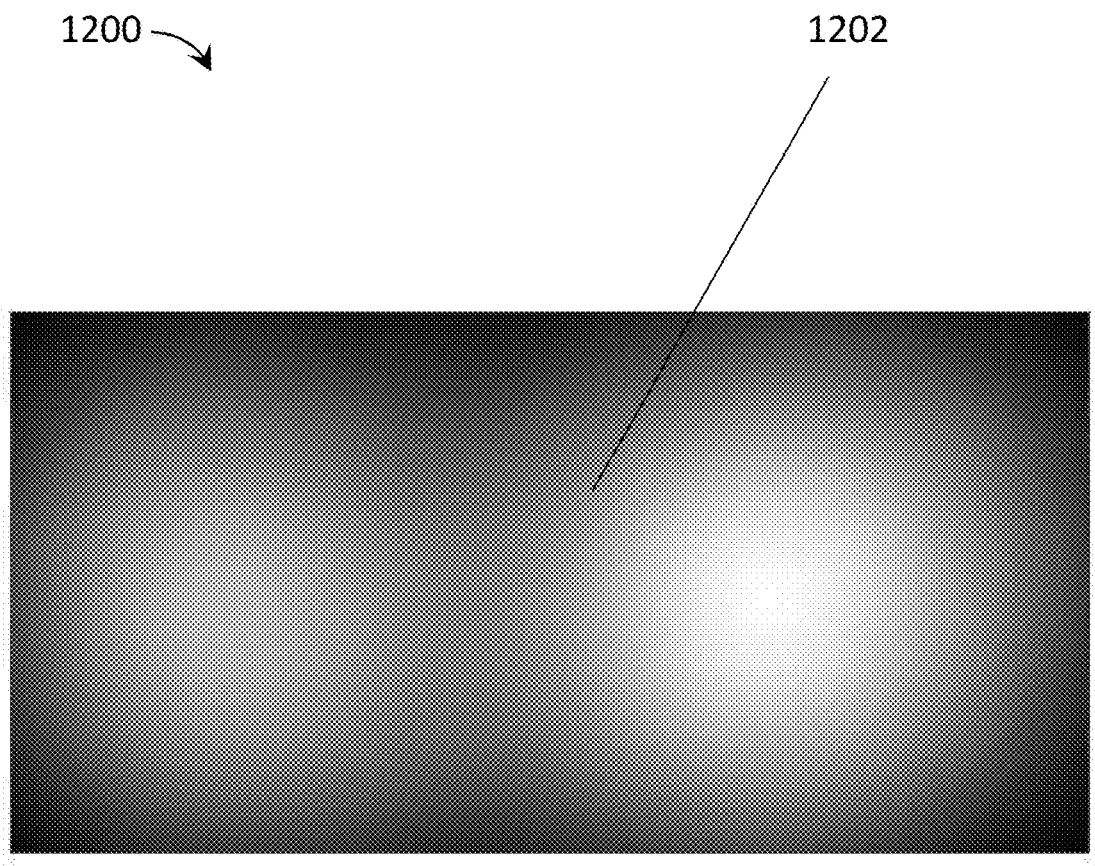
FIG. 12 shows output 1200 for the wide-angle kernel 1102.
Figure 13:
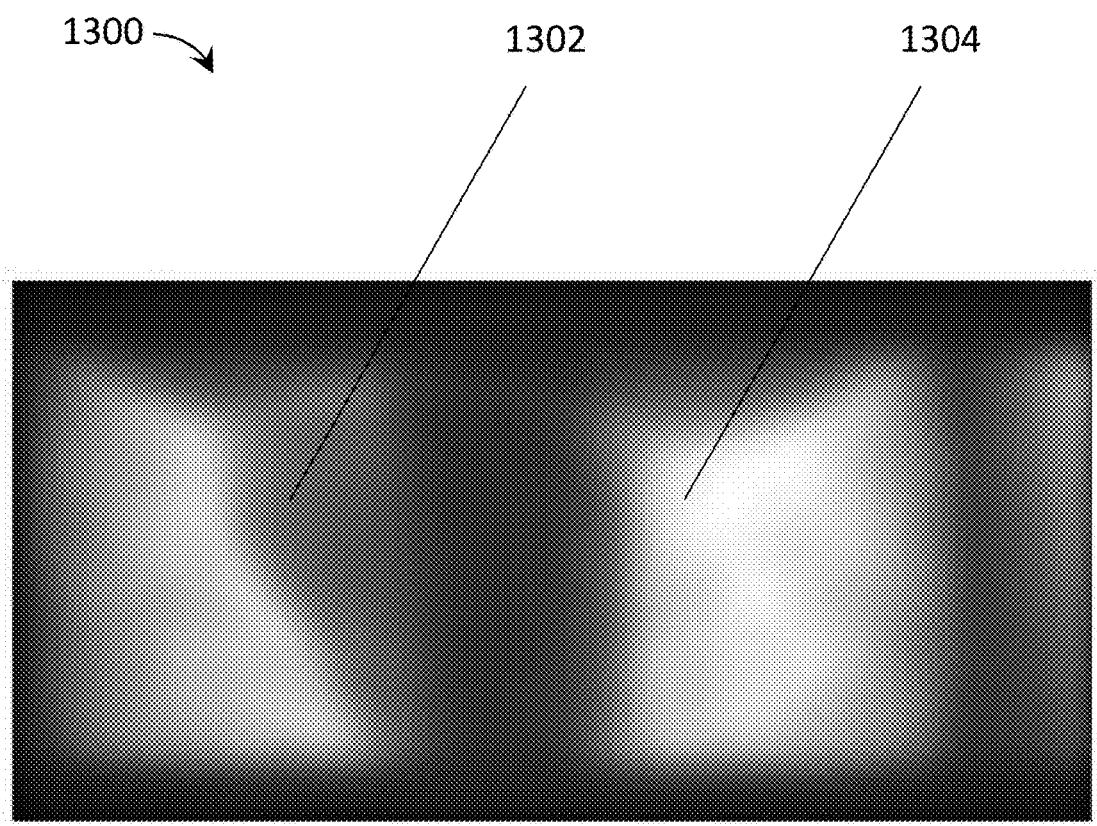
FIG. 13 shows output 1300 for the narrow-angle kernel 1104.

In step 616, algorithm 600 creates a scatter basis by rebuilding the model 600a basis functions, e.g. from the convolution of scatter kernels with the image data in step 614. FIG. 12 shows the output 1200 of this process for the wide-angle kernel 1102. Wide angle kernel convolution creates an output 1200 with low variation 1202 across the image. FIG. 13 shows the output 1300 of this process for the narrow-angle kernel 1104. As shown in FIG. 13, convolving with the narrow angle kernel creates local maxima 1302 and 1304 near low attenuation regions of the image. Outputs 1200 and 1300 comprise an exemplary model basis 600a.

Figure 14:
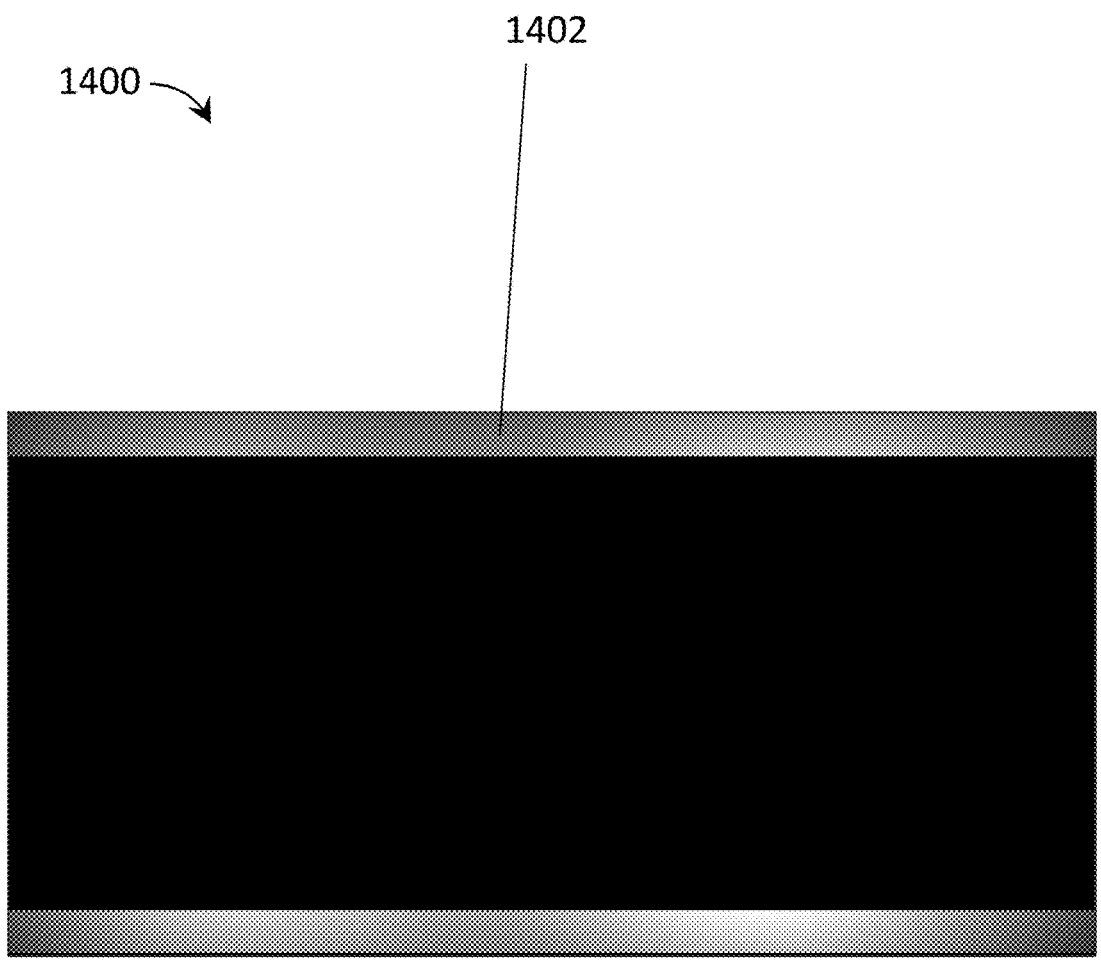
FIG. 14 shows the result 1400 of applying secondary mask 800b to output 1200 for the wide angle scatter kernel 3202.
Figure 15:
FIG. 15 shows the result 1500 of applying secondary mask 800b to output 1300 for the narrow angle scatter kernel 1104.

In step 616, the secondary mask 800b can be applied to the convolved image data outputs 1200 and 1300 from step 616. FIG. 14 shows the result 1400 of applying secondary mask 800b to output 1200 for the wide angle scatter kernel 3202. As shown in FIG. 14, influence of wide angle kernel maximum 1202 is visible in masked image 1400. FIG. 15 shows the result 1500 of applying secondary mask 800b to output 1300 for the narrow angle scatter kernel 1104. FIG. 15 shows the influence of the two maxima 1302 and 1304 from the narrow angle kernel in masked image 1500.

In step 616, the secondary region (A and B) model 600a bases 1 . . . N are vectorized and added to a matrix (A). The bases are weighted by scalars $x_1$ . . . $x_N$ (x). The weighted bases are then summed (Ax). More specifically, the secondary image can be vectorized into the data vector (b) via the following equation:

$$Ax=b \qquad (1)$$

In step 616, equation (1) may be weighted by a weighting matrix (W):

$$WAx=Wb \qquad (2)$$

Here the weighting W may have similar function as in step 612 above, i.e., to emphasize or de-emphasize certain image features. Alternatively, the weighting W may correspond to known experimental features or features in the image acquisition setup (e.g., setup 300). Such features include the energy and width of the incident beam, detector parameters, certain aspects of the collimator 320 or source 306, etc. Weighting may also or alternatively emphasize detector 302 geography (e.g., by favoring data nearer to the primary region C). It may also or alternatively penalize certain characteristics of the data (e.g., higher counts in the secondary regions A/B that may not be due to scatter). In exemplary implementations, image data I in this step can be inversely self-weighted. This can penalize high counts to, for example, discourage overestimation of the scatter amplitude.

In step 626, the system of equations x in equation (3) can be solved for a scatter estimate ($\hat{x}$). The solution can be determined in any number of suitable ways, including via regression techniques, machine learning techniques, various types of neural networks (e.g., convolutional), and may include other techniques such as singular value decomposition or an eigenvalue decomposition. One such exemplary method is a weighted least squares (WLS) solution estimate ($\hat{x}$). This estimate $\hat{x}$ represents the model components (e.g., GMM components) appropriate to estimate scatter S using equation (1) above.

In step 628, an estimated scatter image ($\hat{S}$) is calculated as the sum of the fitted scatter kernel convolutions ($K\hat{x}$):

$$\hat{S}=K\hat{x} \qquad (3)$$

where K is the scatter model basis. K is similar to A, but having domain of the entire image, whereas A may be iterating over column areas of the image. Ŝ can be used to estimate scatter for interpreting the original image frame I (700).

In step 630, solution estimate Ŝ from step 626 can be modified for the original image frame I, and specifically so that output data matches a pixel size of input data. For example, Ŝ may be reshaped to a 2D image. Ŝ may also be up sampled to the original frame I (700) resolution to reverse down sampling described in step 602 above.

Figure 16:
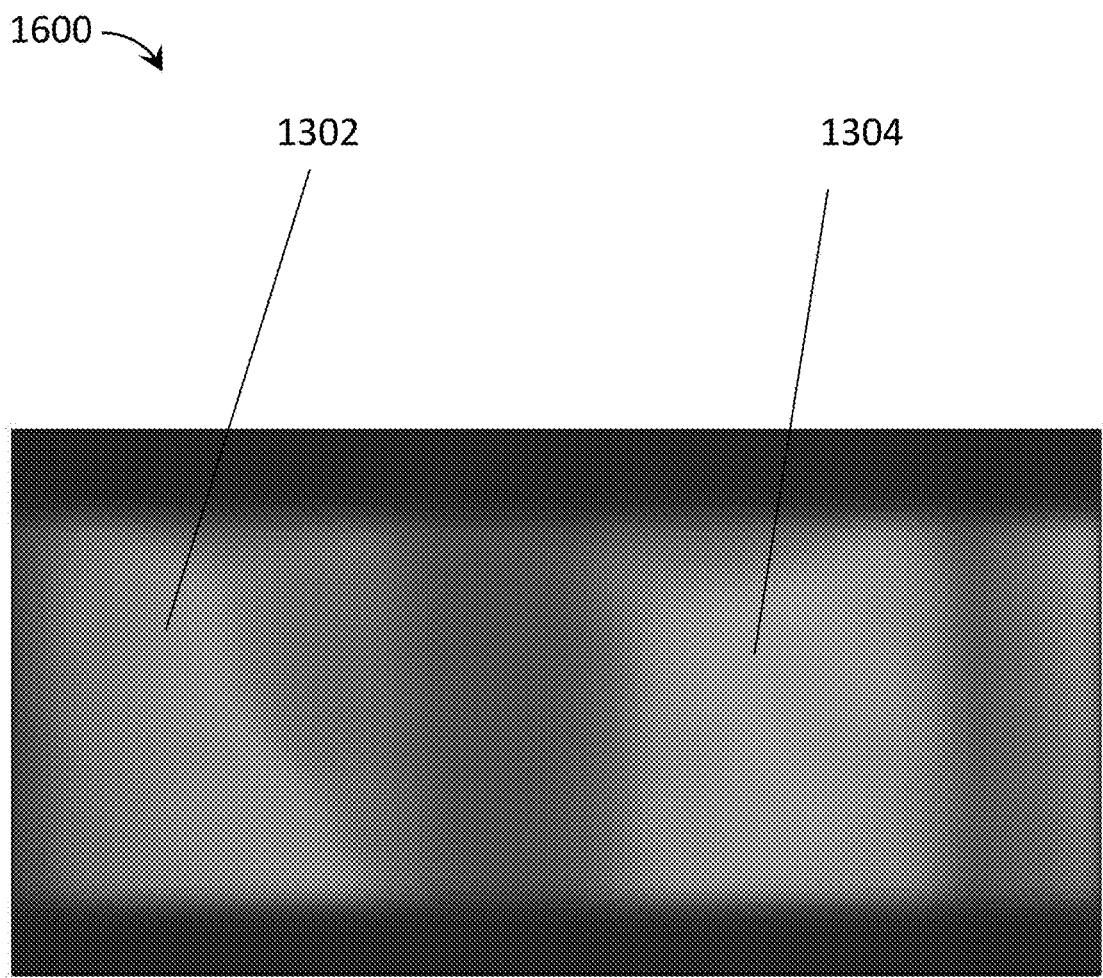
FIG. 16 shows an overall estimated scatter image 1600 produced by algorithm 600.

In step 632, the algorithm 600 produces an overall estimated scatter image 1600 shown in FIG. 16. Once the model is configured, in this case the kernel amplitudes $\hat{x}$ are estimated, then the model is applied to the primary image C to obtain the estimated scatter image Ŝ.

In step 634, the algorithm 600 uses scatter image 600 to modify the originally input image 700. One way scatter image 600 may be used in this step is to eliminate scatter in image 700 by subtracting scatter image 600 from it. Other ways of addressing scatter in image 700 using scatter image 600 are also possible. For example, select portions of scatter image 600 may be subtracted from image 700. The select portions may correspond to image regions of particularly high scatter.

Figure 17:
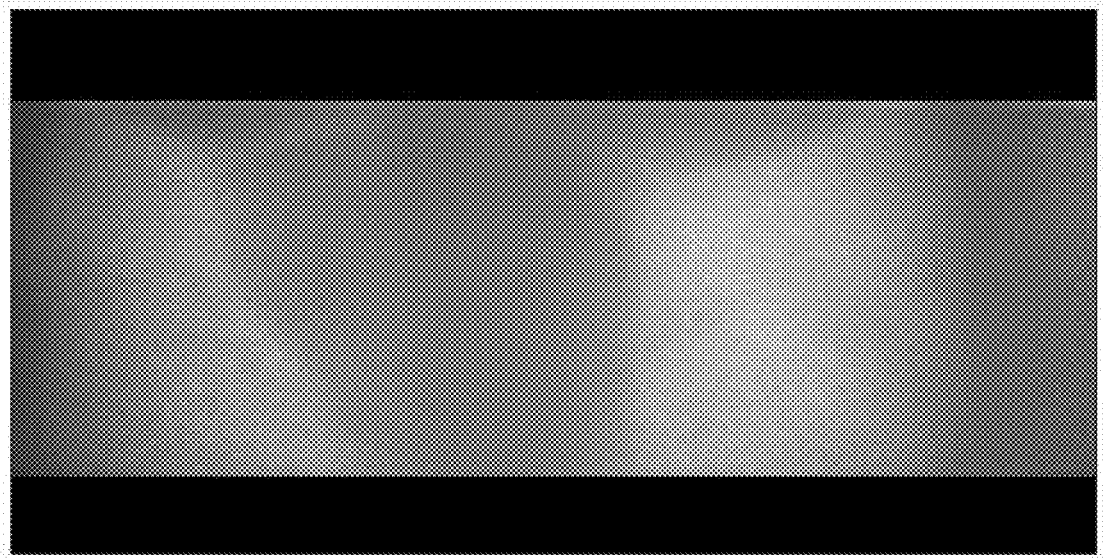
FIG. 17 shows a measurement of scatter in the primary region for comparison with the estimated scatter image 1600.

FIG. 17 shows a measured scatter image 1700 that can be directly compared with the scatter estimate image 1600 in FIG. 16. As can be seen by the comparison, the scatter estimate 1600 shows qualitative agreement with the measured scatter 1700.

A generalized operator representation of the mathematics of method 600 in certain variations is illustrated below.

In step 632, a scatter image component, $I_S$, can be approximated by an operator, $\mathcal{F}$, acting on a one- or two-dimensional primary x-ray projection, $I_P$, after radiating through the object of interest (e.g., the patient, phantom, or other object to be imaged):

$$\mathcal{F}\{I_P\} \approx I_S \qquad (4)$$

A measurement image, $I_M$, by an x-ray detector may include primary (C) image ($I_P$) and secondary (A/B) image components ($I_S$). $I_M$ may be represented by image I discussed above or image 700 shown in FIG. 7, for example. Secondary image components (A/B) may include scattered x-rays and extra-focal source radiation. The measured image is a sum of its primary and secondary components:

$$I_M \approx I_P + I_S \qquad (5)$$

The measured image $I_M$ may include one or more areas shadowed by a beam blocking device (e.g., collimator 320) on the source side 306 of the object. These areas are denoted by the set of pixel locations $\bar{r}_S$. Unblocked pixels are denoted by the set of pixel locations $\bar{r}_P$. The measured image is approximately equal to the scatter component in the blocked region.

$$I_M|_{\bar{r}_S} = I_{\overline{M}} \approx I_{\overline{S}} \qquad (6)$$

An estimate of the scatter signal component, $\hat{I}_S$ (step 632), can be obtained by applying the operator $\mathcal{F}$ to the measured image $I_M$:

$$\mathcal{F}\{I_M\} = \hat{I}_S \qquad (7)$$

The estimated primary image $\widehat{I_P}$ can be estimated by removal of the estimated scatter component $\hat{I}_S$ (step 634):

$$\widehat{I_P} = I_M - \hat{I}_S \qquad (8)$$

For large scatter-to-primary signal ratios (SPR), the method 600 may be iterated or corrected by $-\mathcal{F}\{\hat{I}_S\}$ A modeled operator may consider parametric degrees of freedom, denoted here as vectorized unknowns x. Those parameters may then be optimized over the beam-blocked region $\overline{S}$ upon fitting the measured image data to the modeled scatter data (step 626):

$$\mathcal{F}\{I_M, x\} = \hat{I}_S \qquad (9)$$

$$\min_x |\hat{I}_S - I_S|_{\bar{r}_S} \qquad (10)$$

$$\min_x |\mathcal{F}\{I_M, x\} - I_S|_{\bar{r}_S} \qquad (11)$$

In one variation of the operator $\mathcal{F}$, a set of scatter kernels includes a finite number of Gaussian generating functions, each Gaussian generating function parameterized by variance $\sigma_i^2$ and amplitude $A_i$. Convolution of each kernel with the primary or measured image produces a component of the operator also known as a Gaussian Mixture Model (GMM) in one variation of model 600a (step 614). Amplitude and variance parameters may be either optimized or fixed a priori, for example by calibration or simulation:

$$\mathcal{F}\{I_M, x\} = \sum_{i=1}^{N} [\mathcal{G}(A_i, \sigma_i^2) * I_P] \qquad (12)$$

Multiple variations of operator $\mathcal{F}$ are possible within the above framework (i.e., method 600 and equations 4-12). For example, in operator $\mathcal{F}$ the Gaussian kernels may be replaced with any other generating filter type. Operator $\mathcal{F}$ may include an image transformation to an orthonormal basis, such as Fourier Transform, from which a scatter estimate may be produced from weighted recombination or finite selection of basis functions. Operator $\mathcal{F}$ may include an image transformation to a wavelet basis, such as the Continuous Wavelet Transform (CWT), from which a scatter estimate may be produced from weighted recombination or finite selection of wavelets. Operator $\mathcal{F}$ may include an image decomposition such as singular value decomposition (SVD) or eigen analysis, with scatter image estimate formed by re-composition of a truncated or finite selection of basis components. Input to operator $\mathcal{F}$ may include a set of training data, or a network trained from same, such as Convolutional Neural Net (CNN). The input training data may contain pairs of primary or measured images including a beam-block region and the corresponding scatter images.

It is to be understood that steps 602-634 of algorithm 600 represent a serial process to be performed on each image frame I (700) of a series of images acquired by system 300. Once the algorithm 600 is performed for each image frame I, the image frames can be reconstructed to form a 3D image of the affected area of the patient. The scatter correction may also benefit radiography applications. Algorithm 600 may be performed simultaneously for multiple image frames at the same time. In fact, a collection of image frames may all be run at once. This may produce the end result more quickly. In addition, algorithm 600 may use features of certain image frames in the analysis of features of other image frames when processing is simultaneous and/or concurrent. In other variations, certain parameters relating to analysis of one image frame may be stored and used in the analysis of other image frames, even where the multiple frame analysis is not simultaneous or concurrent.

Although the disclosed technology has been shown and described with respect to a certain aspect, variation or variations, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, variation or variations of the disclosed technology. In addition, while a particular feature of the disclosed technology may have been described above with respect to only one or more of several illustrated aspects or variations, such feature may be combined with one or more other features of the other variations, as may be desired and advantageous for any given or particular application.

While the variations discussed herein have been related to the systems and methods discussed above, these variations are intended to be exemplary and are not intended to limit the applicability of these variations to only those discussions set forth herein. While the present invention has been illustrated by the description of variations thereof, and while the variations have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging apparatus, comprising:
   a radiation source for emitting radiation;
   a radiation detector positioned to receive radiation emitted by the radiation source and generate radiation data, wherein the radiation data comprises a primary component and a secondary component;
   a data processing system configured to:
      receive the radiation data;
      separate the radiation data into the primary and secondary components;
      apply image transforms to at least one of the primary and secondary components using at least one of generating functions and basis decomposition;
      build a scatter model basis using the image transforms;
      adjust parameters in the scatter model to fit scatter in the primary component using the scatter model basis;
      generate an estimated scatter image by using the fitted scatter model; and
      modify the radiation data using the scatter image to decrease the scatter in the radiation data thereby generating a scatter corrected image.

2. The imaging apparatus of claim 1, wherein:
   the radiation source comprises a rotating x-ray source emitting a radiation beam;
   the radiation detector comprises an x-ray detector positioned to receive the radiation from the x-ray source; and
   the apparatus further comprises:
      a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer.

3. The imaging apparatus of claim 2, wherein estimating the scatter component of the radiation data is based on measured scatter data in at least one shadow region.

4. The imaging apparatus of claim 1, wherein modifying the radiation data using the scatter image to decrease the scatter in the radiation data comprises subtracting the scatter image from the radiation data.

5. The imaging apparatus of claim 1, wherein the generating functions comprise at least one of:
   a narrow-angle kernel;
   a wide-angle kernel;
   a gaussian kernel;
   at least one of a filter and a bank of filters;
   an orthonormal basis;
   a Fourier Transform;
   a wavelet basis; and
   a continuous wavelet transform.

6. The imaging apparatus of claim 1, wherein the scatter model comprises a convolutional neural net.

7. The imaging apparatus of claim 1, wherein the scatter model comprises a singular value decomposition or an eigenvalue decomposition.

8. The imaging apparatus of claim 1, wherein the scatter model comprises at least one of a least squares, weighted least squares, conjugate-gradient least squares, steepest descent, and non-linear optimization technique.

9. The imaging apparatus of claim 1, wherein the scatter model basis comprises an orthonormal basis.

10. The imaging apparatus of claim 1, wherein the scatter model basis comprises Gaussian kernels convolved with the primary image.

11. The imaging apparatus of claim 1, wherein the scatter model basis comprises the primary image convolved with at least one of asymmetric Gaussian kernels, symmetric Gaussian kernels and Gaussian kernels with non-zero skewness.

12. The imaging apparatus of claim 1, wherein separating the radiation data into the primary and scatter components comprises filtering the radiation data.

13. The imaging apparatus of claim 1, wherein separating the radiation data into the primary and scatter components comprises segmenting the radiation data.

14. The imaging apparatus of claim 1, wherein adjusting parameters in the scatter model to fit scatter comprises an iterative analysis of the radiation data.

15. The imaging apparatus of claim 14, wherein the iterative analysis analyzes a segmented image comprising primary radiation data.

16. The imaging apparatus of claim 1, wherein the data processing system is configured to offset the radiation data.

17. The imaging apparatus of claim 1, wherein the data processing system is configured to correct the radiation data.

18. The imaging apparatus of claim 1, wherein the data processing system is configured to at least one of normalize the radiation data and weight one or more portions of the radiation data.

19. The imaging apparatus of claim 16, wherein the correction comprises adjusting gain for a portion of the radiation data.

20. The imaging apparatus of claim 1, further including dynamic positioning of collimators to manipulate the radiation emitted by the radiation source prior to the radiation detector receiving the radiation.

21. A method of processing radiation data acquired by a radiological imaging apparatus, comprising:
   receiving the radiation data;
   separating the radiation data into the primary and secondary components;
   applying image transforms to at least one of the primary and secondary components using generating functions;
   building a scatter model basis using the transforms;
   adjusting parameters in the scatter model to fit scatter in the at least one of the primary and secondary components using the scatter model basis;
   generating an estimated scatter image by using the fitted scatter model; and
   modifying the radiation data using the scatter image to decrease the scatter in the radiation data thereby generating a scatter corrected image.

* * * * *